(12) United States Patent
Moqrich et al.

(10) Patent No.: US 9,884,088 B2
(45) Date of Patent: Feb. 6, 2018

(54) TAFA4 COMPOUNDS AND USES THEREOF FOR TREATING PAIN

(71) Applicants: CENTRE NATIONAL DE LA RECHERCHE SCIENTIFIQUE, Paris (FR); UNIVERSITE D'AIX-MARSEILLE, Marseilles (FR)

(72) Inventors: Aziz Moqrich, Marseilles (FR); Marie-Claire Delfini, Marseilles (FR); Annabelle Mantilleri, Apt (FR)

(73) Assignees: CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 0 days.

(21) Appl. No.: 14/787,483

(22) PCT Filed: May 6, 2014

(86) PCT No.: PCT/EP2014/059247
§ 371 (c)(1),
(2) Date: Oct. 28, 2015

(87) PCT Pub. No.: WO2014/180853
PCT Pub. Date: Nov. 13, 2014

(65) Prior Publication Data
US 2016/0113996 A1    Apr. 28, 2016

(30) Foreign Application Priority Data
May 6, 2013 (EP) .................................... 13305592

(51) Int. Cl.
| | | |
|---|---|---|
| A61K 38/00 | (2006.01) | |
| A61P 23/00 | (2006.01) | |
| A61K 38/17 | (2006.01) | |
| A01K 67/027 | (2006.01) | |
| C07K 14/47 | (2006.01) | |

(52) U.S. Cl.
CPC ...... *A61K 38/1709* (2013.01); *A01K 67/0276* (2013.01); *C07K 14/47* (2013.01); *A01K 2217/077* (2013.01); *A01K 2227/105* (2013.01); *A01K 2267/0356* (2013.01)

(58) Field of Classification Search
CPC .. A61K 38/1709; C07K 14/475; C07K 14/47; A01K 67/0276; A01K 2217/077; A01K 2227/105; A01K 2267/0356
USPC ........................................................ 514/1.1
See application file for complete search history.

(56) References Cited

U.S. PATENT DOCUMENTS
2009/0077680 A1    3/2009 Abuin et al.

FOREIGN PATENT DOCUMENTS
WO    WO 2006/013462    2/2006

OTHER PUBLICATIONS

USPTO Sequence search for SEQ ID No. 2 ; Mar. 2016, summary attached p. 1-7.*
Miyamoto, K., etal., "Identification of 20 genes aberrantly methylated in human breast cancers," *International Journal of Cancer*, Sep. 2005, vol. 116, No. 3, pp. 407-414.
Tang, Y.T., et al., "TAFA: a novel secreted family with conserved cysteine residues and restricted expression in the brain," *Genomics*, Apr. 1, 2004, vol. 83, No. 4, pp. 727-734.

* cited by examiner

*Primary Examiner* — Christopher M Babic
*Assistant Examiner* — Kelaginamane T Hiriyanna
(74) *Attorney, Agent, or Firm* — Saliwanchik, Lloyd & Eisenschenk

(57) ABSTRACT

The present invention relates to a method of using a TAFA4 protein or an agonist thereof for preventing, alleviating or treating pain in a subject. In one embodiment, the invention provides a method of treating pain in a subject by administering a TAFA4 protein or an agonist thereof to the subject. The TAFA4 can have the amino acid sequence of SEQ ID NO: 1 or 2 or a sequence having at least 90% sequence identity to SEQ ID NO: 1 or 2. The TAFA4 agonist can also be a peptide comprising 10 to 60 consecutive amino acid residues of SEQ ID NO: 1 or 2. Also described herein are pharmaceutical compositions, their preparation and uses as well as methods for preventing, alleviating or treating pain using such compounds and compositions.

Figure 1:
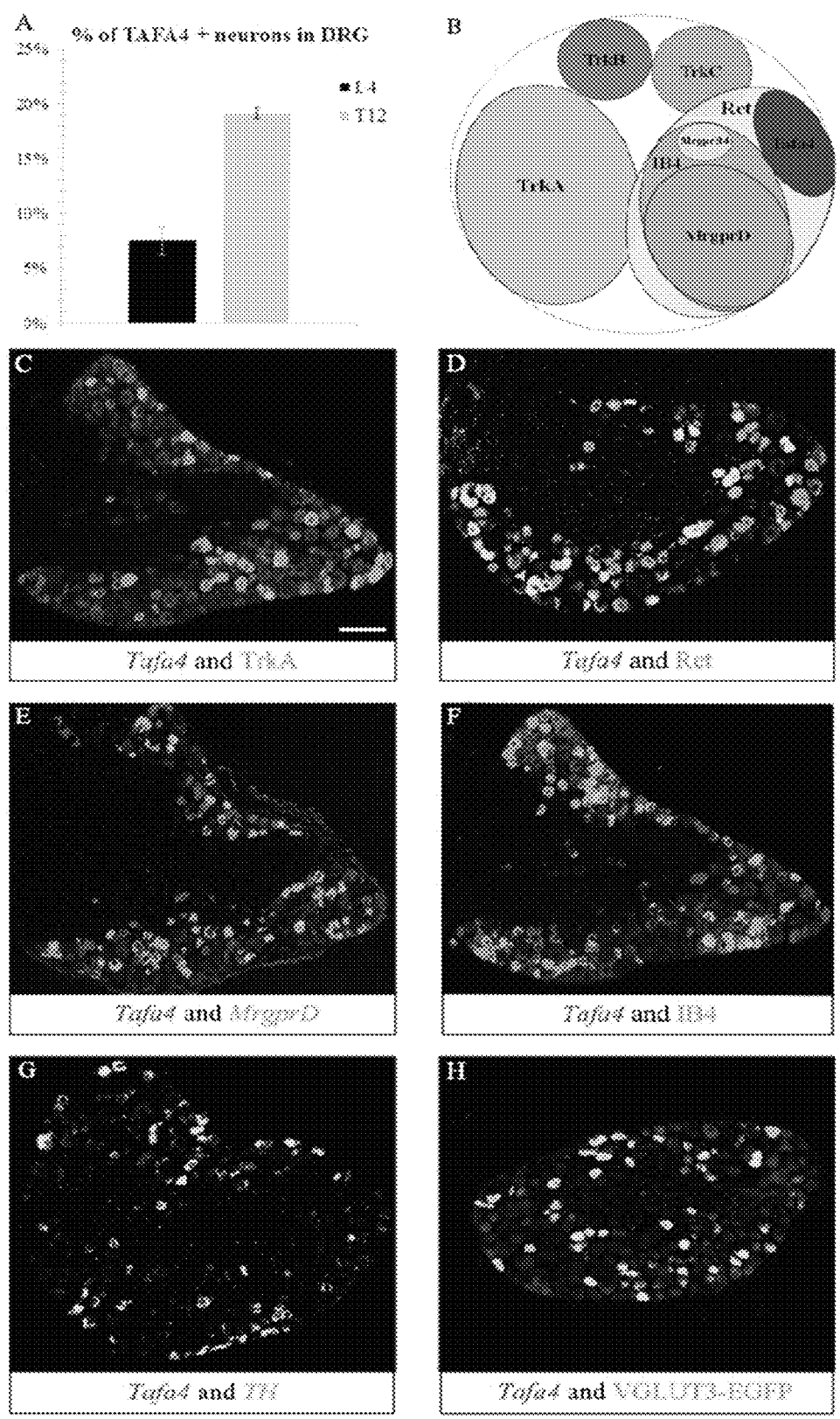

10 Claims, 18 Drawing Sheets
(12 of 18 Drawing Sheet(s) Filed in Color)

F  Mechanically activated cation currents

G  Mechanically triggeral AP

SEQUENCE LISTING

```
<160> NUMBER OF SEQ ID NOS: 30

<210> SEQ ID NO 1
<211> LENGTH: 79
<212> TYPE: PRT
<213> ORGANISM: Homo sapiens
<220> FEATURE:
<221> NAME/KEY: MISC_FEATURE
<223> OTHER INFORMATION: human TAFA4 protein

<400> SEQUENCE: 1

His Arg Gly His Ala Gly His His Lys Gly Thr Cys Val Val Ala Val
1               5                   10                  15

His Arg Cys Cys Asn Lys Asn Arg Arg Ser Thr Val Lys Cys Ser Cys
            20                  25                  30

Gly Val Ala Gly Thr Thr Arg Ala Ser Cys Val Ala Ser Val Lys Trp
        35                  40                  45

Trp Cys His Met Asn Cys Gly Asp Cys Lys Val Asp Tyr Ser Gly Trp
    50                  55                  60

Ser Cys Ser Ser Gly Asn Lys Val Lys Thr Thr Lys Val Thr Arg
65                  70                  75

<210> SEQ ID NO 2
<211> LENGTH: 104
<212> TYPE: PRT
<213> ORGANISM: Mus musculus
<220> FEATURE:
<221> NAME/KEY: MISC_FEATURE
<223> OTHER INFORMATION: mouse TAFA4 protein

<400> SEQUENCE: 2

Gln His Leu Arg Gly His Ala Gly His His Leu Ile Lys Pro Gly Thr
1               5                   10                  15

Cys Glu Val Val Ala Val His Arg Cys Cys Asn Lys Asn Arg Ile Glu
            20                  25                  30

Glu Arg Ser Gln Thr Val Lys Cys Ser Cys Phe Pro Gly Gln Val Ala
        35                  40                  45

Gly Thr Thr Arg Ala Gln Pro Ser Cys Val Glu Ala Ala Ile Val Ile
    50                  55                  60

Glu Lys Trp Trp Cys His Met Asn Pro Cys Leu Glu Gly Glu Asp Cys
65                  70                  75                  80

Lys Val Leu Pro Asp Ser Ser Gly Trp Ser Cys Ser Ser Gly Asn Lys
                85                  90                  95

Val Lys Thr Thr Lys Val Thr Arg
            100

<210> SEQ ID NO 3
<211> LENGTH: 25
<212> TYPE: PRT
<213> ORGANISM: Artificial Sequence
<220> FEATURE:
<223> OTHER INFORMATION: TAFA4 agonist, 25aa peptide, N-terminus of
      human TAFA4 protein

<400> SEQUENCE: 3
```

-continued

```
His Arg Gly His Ala Gly His His Lys Gly Thr Cys Val Val Ala Val
1               5                   10                  15

His Arg Cys Cys Asn Lys Asn Arg Arg
            20                  25

<210> SEQ ID NO 4
<211> LENGTH: 27
<212> TYPE: PRT
<213> ORGANISM: Artificial Sequence
<220> FEATURE:
<223> OTHER INFORMATION: TAFA4 agonist, 27aa peptide, C-terminus of
      human TAFA4 protein

<400> SEQUENCE: 4

Asn Cys Gly Asp Cys Lys Val Asp Tyr Ser Gly Trp Ser Cys Ser Ser
1               5                   10                  15

Gly Asn Lys Val Lys Thr Thr Lys Val Thr Arg
            20                  25

<210> SEQ ID NO 5
<211> LENGTH: 22
<212> TYPE: DNA
<213> ORGANISM: Artificial Sequence
<220> FEATURE:
<223> OTHER INFORMATION: primer tafa4-F1

<400> SEQUENCE: 5
tgctcagaag ttcatagcca aa                                             22

<210> SEQ ID NO 6
<211> LENGTH: 22
<212> TYPE: DNA
<213> ORGANISM: Artificial Sequence
<220> FEATURE:
<223> OTHER INFORMATION: primer tafa4-R1

<400> SEQUENCE: 6
taaaggaaca tttgcaagct ca                                             22

<210> SEQ ID NO 7
<211> LENGTH: 15
<212> TYPE: DNA
<213> ORGANISM: Artificial Sequence
<220> FEATURE:
<223> OTHER INFORMATION: primer tafa4-F2

<400> SEQUENCE: 7
atatgtgcag tgtgg                                                     15

<210> SEQ ID NO 8
<211> LENGTH: 35
<212> TYPE: DNA
<213> ORGANISM: Artificial Sequence
<220> FEATURE:
<223> OTHER INFORMATION: primer tafa4-R2+T7

<400> SEQUENCE: 8
taatacgact cactataggg cagccaagtt caaac                               35

<210> SEQ ID NO 9
<211> LENGTH: 22
<212> TYPE: DNA
<213> ORGANISM: Artificial Sequence
<220> FEATURE:
<223> OTHER INFORMATION: primer TH-F1
```

```
<400> SEQUENCE: 9
aagccaaaat ccaccactta ga                                              22

<210> SEQ ID NO 10
<211> LENGTH: 22
<212> TYPE: DNA
<213> ORGANISM: Artificial Sequence
<220> FEATURE:
<223> OTHER INFORMATION: primer TH-R1

<400> SEQUENCE: 10
ccgtggagag tttttcaatt tc                                              22

<210> SEQ ID NO 11
<211> LENGTH: 42
<212> TYPE: DNA
<213> ORGANISM: Artificial Sequence
<220> FEATURE:
<223> OTHER INFORMATION: primerTH-R2+T7

<400> SEQUENCE: 11
taatacgact cactataggg agagatgcaa gtccaatgtc ct                        42

<210> SEQ ID NO 12
<211> LENGTH: 22
<212> TYPE: DNA
<213> ORGANISM: Artificial Sequence
<220> FEATURE:
<223> OTHER INFORMATION: primer Vglut3-F1

<400> SEQUENCE: 12
tagctcagtt tccaggaatg gt                                              22

<210> SEQ ID NO 13
<211> LENGTH: 26
<212> TYPE: DNA
<213> ORGANISM: Artificial Sequence
<220> FEATURE:
<223> OTHER INFORMATION: primer Vglut3-R1

<400> SEQUENCE: 13
ggagatctaa caacatctga taacac                                          26

<210> SEQ ID NO 14
<211> LENGTH: 22
<212> TYPE: DNA
<213> ORGANISM: Artificial Sequence
<220> FEATURE:
<223> OTHER INFORMATION: primer Vglut3-F2

<400> SEQUENCE: 14
cccccTagag tatcaggaat tt                                              22

<210> SEQ ID NO 15
<211> LENGTH: 47
<212> TYPE: DNA
<213> ORGANISM: Artificial Sequence
<220> FEATURE:
<223> OTHER INFORMATION: primer Vglut3-R2+T7

<400> SEQUENCE: 15
taatacgact cactataggg tgggaagttt taaaaatcta tgattag                   47

<210> SEQ ID NO 16
```

<211> LENGTH: 20
<212> TYPE: DNA
<213> ORGANISM: Artificial Sequence
<220> FEATURE:
<223> OTHER INFORMATION: primer TrkB-F1

<400> SEQUENCE: 16
ctgagagggc cagtcacttc                                          20

<210> SEQ ID NO 17
<211> LENGTH: 20
<212> TYPE: DNA
<213> ORGANISM: Artificial Sequence
<220> FEATURE:
<223> OTHER INFORMATION: primer TrkB-R1

<400> SEQUENCE: 17
catggcaggt caacaagcta                                          20

<210> SEQ ID NO 18
<211> LENGTH: 20
<212> TYPE: DNA
<213> ORGANISM: Artificial Sequence
<220> FEATURE:
<223> OTHER INFORMATION: primer TrkB-F2

<400> SEQUENCE: 18
cagtgggtct cagcacagaa                                          20

<210> SEQ ID NO 19
<211> LENGTH: 40
<212> TYPE: DNA
<213> ORGANISM: Artificial Sequence
<220> FEATURE:
<223> OTHER INFORMATION: primer TrkB-R2+T7

<400> SEQUENCE: 19
taatacgact cactataggg ctaggaccag gatggctctg                    40

<210> SEQ ID NO 20
<211> LENGTH: 22
<212> TYPE: DNA
<213> ORGANISM: Artificial Sequence
<220> FEATURE:
<223> OTHER INFORMATION: primer MrgprD-F1

<400> SEQUENCE: 20
gggcatcaac tggttcttac tc                                       22

<210> SEQ ID NO 21
<211> LENGTH: 20
<212> TYPE: DNA
<213> ORGANISM: Artificial Sequence
<220> FEATURE:
<223> OTHER INFORMATION: primer MrgprD-R1

<400> SEQUENCE: 21
agggattgtc ttgactgtcg                                          20

<210> SEQ ID NO 22
<211> LENGTH: 22
<212> TYPE: DNA
<213> ORGANISM: Artificial Sequence
<220> FEATURE:
<223> OTHER INFORMATION: primer MrgprD-F2

<400> SEQUENCE: 22

```
aacgggatgt gaggctactt ta                                              22

<210> SEQ ID NO 23
<211> LENGTH: 42
<212> TYPE: DNA
<213> ORGANISM: Artificial Sequence
<220> FEATURE:
<223> OTHER INFORMATION: primer MrgprD-R2+T7

<400> SEQUENCE: 23
taatacgact cactataggg atttatgcct tgacttccct ga                        42

<210> SEQ ID NO 24
<211> LENGTH: 20
<212> TYPE: DNA
<213> ORGANISM: Artificial Sequence
<220> FEATURE:
<223> OTHER INFORMATION: primer SCG10-F1

<400> SEQUENCE: 24
gcaatggcct acaaggaaaa                                                 20

<210> SEQ ID NO 25
<211> LENGTH: 20
<212> TYPE: DNA
<213> ORGANISM: Artificial Sequence
<220> FEATURE:
<223> OTHER INFORMATION: primer SCG10-R1

<400> SEQUENCE: 25
ggcaggaagc agattacgag                                                 20

<210> SEQ ID NO 26
<211> LENGTH: 20
<212> TYPE: DNA
<213> ORGANISM: Artificial Sequence
<220> FEATURE:
<223> OTHER INFORMATION: primer SCG10-F2

<400> SEQUENCE: 26
agcagttggc agagaagagg                                                 20

<210> SEQ ID NO 27
<211> LENGTH: 40
<212> TYPE: DNA
<213> ORGANISM: Artificial Sequence
<220> FEATURE:
<223> OTHER INFORMATION: primer SCG10R2+T7

<400> SEQUENCE: 27
taatacgact cactataggg ggcaggaagc agattacgag                           40

<210> SEQ ID NO 28
<211> LENGTH: 24
<212> TYPE: DNA
<213> ORGANISM: Artificial Sequence
<220> FEATURE:
<223> OTHER INFORMATION: oligonucleotide for genotyping PCR, GFP 436

<400> SEQUENCE: 28
gaagaagtcg tgctgcttca tgtg                                            24

<210> SEQ ID NO 29
<211> LENGTH: 23
<212> TYPE: DNA
```

```
<213> ORGANISM: Artificial Sequence
<220> FEATURE:
<223> OTHER INFORMATION: oligonucleotide for genotyping PCR, 1585

<400> SEQUENCE: 29
ctgtggagga aatggtttca act                                            23

<210> SEQ ID NO 30
<211> LENGTH: 23
<212> TYPE: DNA
<213> ORGANISM: Artificial Sequence
<220> FEATURE:
<223> OTHER INFORMATION: oligonucleotide for genotyping PCR, 1587

<400> SEQUENCE: 30
ctgcaaagag aagccaaagc tac                                            23
```

TAFA4 COMPOUNDS AND USES THEREOF FOR TREATING PAIN

CROSS-REFERENCE TO RELATED APPLICATION

This application is the U.S. national stage application of International Patent Application No. PCT/EP2014/059247, filed May 6, 2014.

The Sequence Listing for this application is labeled "Seq-List.txt" which was created on Oct. 20, 2015 and is 8 KB. The entire contents of the sequence listing is incorporated herein by reference in its entirety.

The present invention relates to novel compounds for use for preventing, alleviating or treating pain in a subject. Also described herein are pharmaceutical compositions, their preparation and uses as well as methods for preventing, alleviating or treating pain using such compounds and compositions.

BACKGROUND OF THE INVENTION

Pain is an unpleasant sensory experience associated with actual or potential tissue damage. Thus, pain is the most common symptom of various injuries and diseases. There exist different classifications of pain, for example, nociceptive pain, inflammatory pain associated with tissue damage and the infiltration of immune cells, and pathological pain, which is a disease state caused by damage to the nervous system (i.e., neuropathic pain) or by its abnormal function (dysfunctional pain, as in fibromyalgia, irritable bowel syndrome, tension type headache, etc.). Pain is usually transitory, lasting only until the noxious stimulus is removed or the underlying damage or pathology has healed, but some painful conditions, such as rheumatoid arthritis, peripheral neuropathy, cancer and idiopathic pain (pain that persists after the trauma or pathology has healed, or that arises without any apparent cause), may persist for years. Pain that lasts a long time is called chronic, and pain that resolves quickly is called acute. Traditionally, the distinction between acute and chronic pain has relied upon an arbitrary interval of time from onset, the two most commonly used markers being 3 months and 6 months since the onset of pain (Turk, Okifuji, Pain terms and taxonomies of pain; In: Bonica, Loeser, Chapman, Turk, Butler, Bonica's management of pain. Hagerstown: Lippincott Williams & Wilkins, 2001), though some theorists and researchers have placed the transition from acute to chronic pain at 12 months (Spanswick, Main, Pain management: an interdisciplinary approach. Edinburgh: Churchill Livingstone, 2000). Others apply "acute" to pain that lasts less than 30 days, "chronic" to pain of more than six months' duration, and "subacute" to pain that lasts from one to six months (Thienhaus, Cole, Classification of pain. In: Weiner, Pain management: a practical guide for clinicians. Boca Raton: CRC Press, 2002). A popular alternative definition of chronic pain, involving no arbitrarily fixed durations, is "pain that extends beyond the expected period of healing" (Turk, Okifuji, 2001, Pain terms and taxonomies. In Loeser, Butler, Chapman, et al. Bonica's management of pain, Lippincott Williams&Wilkins. ISBN 0-683-30462-3). Chronic pain may be classified as cancer pain or benign (Thienhaus, Cole, 2002, Classification of pain. In Weiner, Pain management: A practical guide for clinicians, American Academy of Pain Management, ISBN 0-8493-0926-3).

Pain sensation is conveyed to the brain by sensory neurons which are also called nociceptors. Nociceptors are considered polymodal since they may respond to multiple forms of noxious or intense stimuli, such as heat, mechanical, and chemical stimuli. Sensory afferent fibers of nociceptors are heterogeneous in many aspects. For example, sensory nerves are classified as Aα, -β, -δ and C-fibers according to their diameter and degree of myelination. Then, sensory inputs from the periphery are processed and conveyed to higher brain regions by complex circuits involving excitatory and inhibitory interneurons within the spinal cord (Basbaum et al., 2009; Todd, 2010). The balance between excitation and inhibition is crucial for maintenance of normal sensory function, and dysfunction of these circuits leads to the development of pain such as inflammatory and neuropathic pain.

Treatment of pain includes the use of local anesthetics, which block neuronal transmission and affect sensation as well as pain, and analgesics, which relieve pain and additionally may interfere with the activity of chemical mediators of inflammation. Acute pain is usually managed with medications such as analgesics and anesthetics. Management of chronic pain, however, is much more difficult.

The effectiveness of analgesics relies on how they are able to block the nerve messages that are sent by the pain receptors to the brain. They further have an effect on the body temperature to increase it (known as fever) or decrease it. Analgesic drugs act in various ways on the peripheral and central nervous systems; they include paracetamol (para-acetylaminophenol, also known as acetaminophen or simply APAP), the non-steroidal anti-inflammatory drugs (NSAIDs) such as the salicylates, and opioid drugs such as morphine and opium.

The exact mechanism of action of paracetamol/acetaminophen is uncertain, but it appears to act centrally rather than peripherally (in the brain rather than in the nerve endings). Aspirin and the other non-steroidal anti-inflammatory drugs (NSAIDs) inhibit cyclooxygenases, leading to a decrease in prostaglandin production. This reduces pain and also inflammation (in contrast to paracetamol and the opioids). Paracetamol has few side effects and is regarded as safe, although intake above the recommended dose can lead to liver damage, which can be severe and life-threatening, and occasionally kidney damage. NSAIDs predispose to peptic ulcers, renal failure, allergic reactions, and occasionally hearing loss, and can increase the risk of hemorrhage by affecting platelet function. The use of aspirin in children under 16 suffering from viral illness has been linked to Reye's syndrome, a rare but severe liver disorder. Morphine, the archetypal opioid, and various other substances (e.g., codeine, oxycodone, hydrocodone, dihydromorphine, pethidine) all exert a similar influence on the cerebral opioid receptor system. Dosing of all opioids may be limited by opioid toxicity (confusion, respiratory depression, myoclonic jerks and pinpoint pupils) and seizures (tramadol), but there is no dose ceiling in patients who accumulate tolerance.

The analgesic choice is also determined by the type of pain: for neuropathic pain, traditional analgesics are less effective, and there is often benefit from classes of drugs that are not normally considered analgesics, such as tricyclic antidepressants and anticonvulsants. Tricyclic antidepressants, especially amitriptyline, have been shown to improve treatment of pain in what appears to be a central manner. Nefopam is used in Europe for pain relief with concurrent opioids. The exact mechanism of carbamazepine, gabapentin and pregabalin is similarly unclear, but these anticonvulsants are used to treat neuropathic pain with differing degrees of success. Anticonvulsants are most commonly used for neuropathic pain as their mechanism of action tends to inhibit pain sensation.

However, certain combination analgesic products can result in significant adverse events, including accidental overdoses, most often due to confusion which arises from the multiple (and often non-acting) components of these combinations (Murnion, Combination analgesics in adults. Australian Prescriber (33):113-5. See Worldwide Website: australianprescriber.com/magazine/33/4/113/5).

Inadequate treatment of pain is widespread throughout surgical wards, intensive care units, accident and emergency departments, in general practice, in the management of all forms of chronic pain including cancer pain, and in end of life care. This neglect is extended to all ages, from neonates to the frail elderly. Improved treatments of pain are highly requested by patients, in particular when considering neuropathic, inflammatory and/or chronic pain for which treatment remains incomplete whatever the selected known analgesic molecule.

SUMMARY OF THE INVENTION

The purpose of the present invention is to provide novel and efficient compositions and methods for treating pain. In particular, the present invention proposes new compositions and methods for preventing or treating pain by modulating neuronal excitability.

An object of the invention more specifically relates to a TAFA4 protein, or an agonist thereof, for use as an active ingredient for treating or preventing pain in a subject.

The invention also relates to a method of preventing or treating pain in a subject, the method comprising administering to a subject in need thereof an effective amount of a TAFA4 protein or an agonist thereof, either alone or in combination with one or more additional active compound(s) efficient against pain.

Another object of the invention relates to a kit comprising i) a TAFA4 protein or an agonist thereof or a composition comprising such a protein or agonist, and ii) at least one additional distinct active compound efficient against pain.

In a particular embodiment, the TAFA4 protein comprises the amino acid sequence of SEQ ID NO: 1 or 2, or a sequence having at least 90% identity to SEQ ID NO: 1 or 2. The agonist preferably comprises a peptide fragment of a TAFA4 protein that modulates excitability of nociceptors or interneurons, preferably C-fiber nociceptors (preferably C-LTMRs) or spinal cord interneurons (preferably spinal cord lamina IIi interneurons). Typically, the agonist is a peptide comprising a fragment of at least 10 consecutive amino acid residues of SEQ ID NO: 1 or 2, preferably of at least 20, 25, 27 or 30 consecutive amino acid residues; more preferably the agonist comprises the amino acid sequence of SEQ ID NO: 3 or 4.

In this regard, a further object of the invention relates to a polypeptide or peptide agonist of a TAFA4 protein. Preferably, the polypeptide agonist comprises a fragment of a TAFA4 protein and modulates excitability of nociceptors or interneurons, preferably C-fiber nociceptors (preferably C-LTMRs) or spinal cord interneurons (preferably spinal cord lamina Iii interneurons).

The invention is suitable for preventing or treating any pain. In particular, it may be used to treat or prevent neuropathic pain, inflammatory pain, nociceptor-mediated pain, acute pain, subacute pain, chronic pain, somatic pain, visceral pain, allodynia, hyperalgesia, or pain associated with a nerve injury. The invention is particularly suited for treating inflammatory and/or neuropathic pain.

The TAFA4 protein or agonist may be administered or applied by any route, such as a topical, oral, anal, intramuscular, intravenous, intraperitoneal, cutaneous, subcutaneous, dermical, transdermic, or intrathecal route.

A further object of the invention relates to a composition comprising a TAFA4 protein or an agonist thereof as described herein and, preferably, a pharmaceutically acceptable carrier.

The TAFA4 compounds of the invention may be used either alone or in further combination with one or several additional active compound(s) or treatment(s). The compounds for use in the present invention may be formulated or administered simultaneously, separately or sequentially.

A further object of this invention relates to a transgenic rodent having a defective TAFA4 gene, more preferably a targeted inactivated TAFA4 gene. Such rodents preferably exhibit an enhanced mechanical and chemical hypersensitivity and enhanced neuronal hyperexcitability.

The invention may be used for treating pain in any mammalian subject, particularly in human subjects.

LEGENDS TO THE FIGURES

The patent or application file contains at least one drawing executed in color. Copies of this patent or patent application publication, with color drawing(s), will be provided by the Office upon request and payment of the necessary fee.

FIG. 1: TAFA4 specifically marks C-LTMRs.

(A) Percentage of TAFA4-positive neurons in L4 (n=3; 7.5%±1.3%) and T12 (n=3; 19.2%±0.5%) DRG of wild-type adult mice.

(B) Schematic representation of DRG Tafa4 expression data. The sizes of the circles in the diagram are roughly proportional to the sizes of the cell populations depicted by the different molecular markers.

(C-H) In situ hybridization for Tafa4 probe in adult mouse lumbar (C-F) and thoracic (G, H) DRG sections followed by immunostaining or in situ hybridization for TrkA (C), cRet (D), MrgprD (E), D34 (fluorescein-conjugated *G. simplicifolia* IB4-lectin) (F), TH (G) and EGFP (H). (Scale bars=100 µm.)

Figure 2:
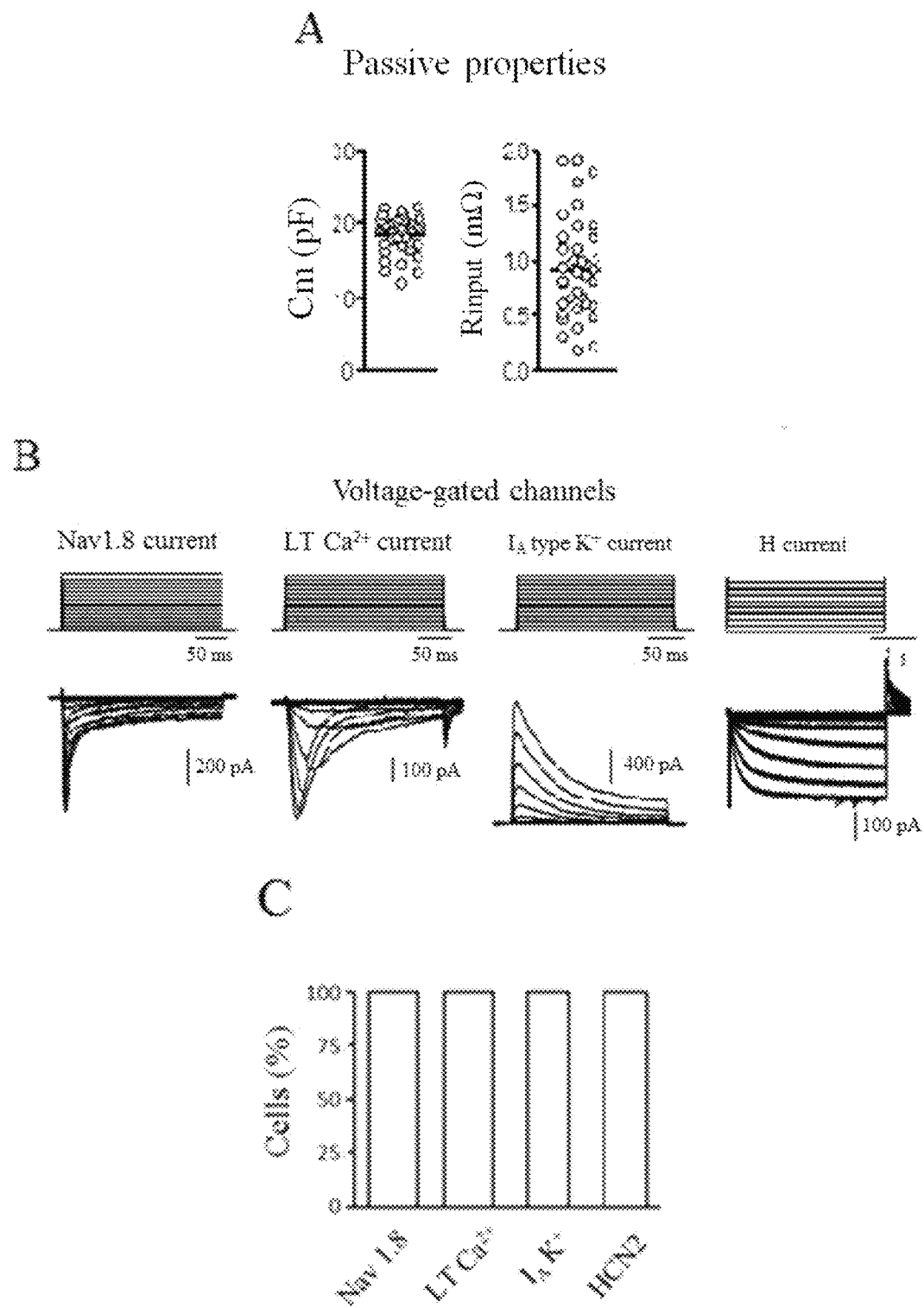
Figure 2:
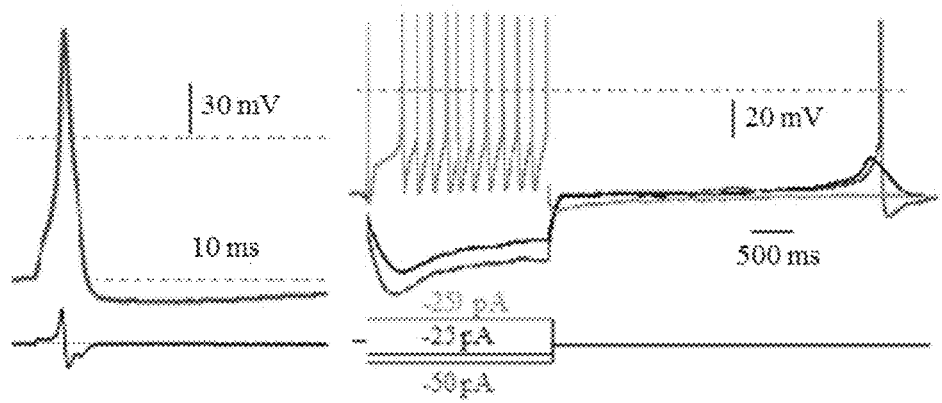
Figure 2:
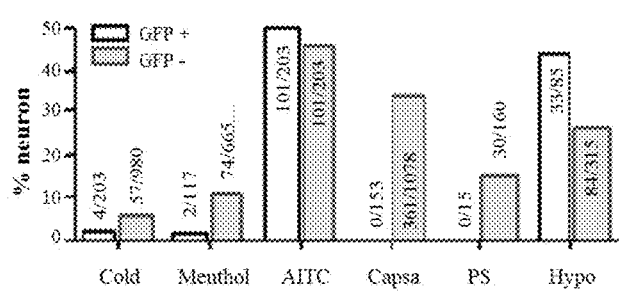
Figure 2:
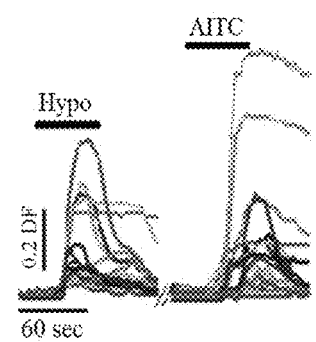
Figure 2:
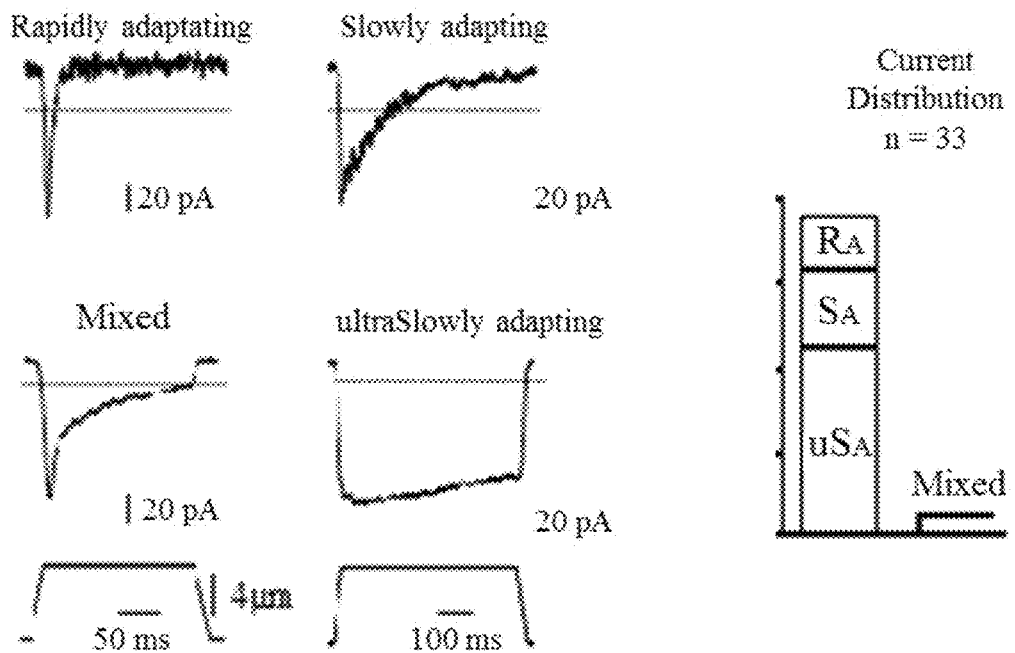
Figure 2:
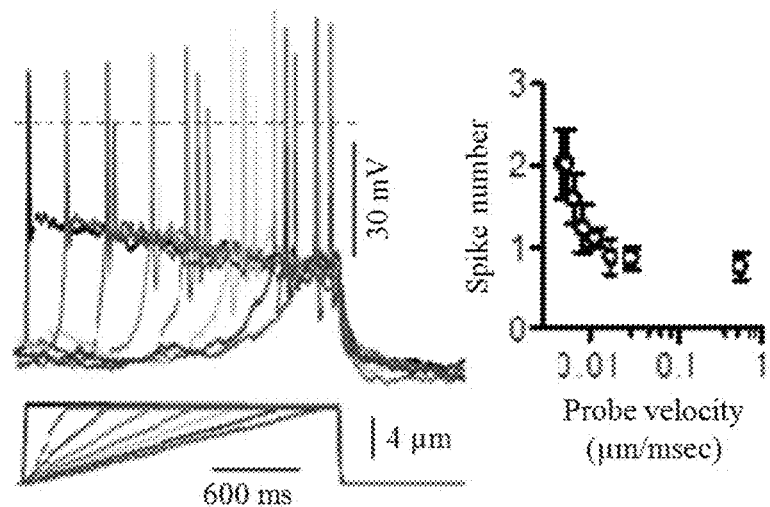

FIG. 2: GFP$^+$ neurons displayed many properties of C-unmyelinated nociceptors.

(A) Dot plots of the cell membrane capacitance (Cm) and input resistance ($R_{input}$) of TAFA4$^{GFP/+}$ (GFP$^+$) neurons.

(B, C) Recordings of isolated Nav1.8-, T-type Ca$^{2+}$, IK$_A$- and h-currents (B) and corresponding frequency histograms (C) in TAFA4$^{GFP/+}$ neurons. Number of neurons tested is indicated.

(D) Representative action potentials and firing responses in TAFA4$^{GFP/+}$ neurons evoked by short 2 ms-depolarizing steps (left panel) or long duration depolarizing and hyperpolarizing steps (right panel). Note Ih-mediated sag on membrane hyperpolarization and the delayed rebound potential triggered by T-type Ca$^{2+}$ current. The dotted line indicates 0 mV level.

(E) Percentage of GFP$^+$-(TAFA4$^{GFP/+}$) and GFP$^-$ neurons that respond to a variety of sensory stimuli (as indicated). Right panel: representative examples of calcium signals evoked in TAFA4$^{GFP/+}$ neurons in response to bath-applied hypotonic solution (200 mOsmol/l) and AITC (100 µM).

(F) Representative traces of MA currents elicited by a standard mechanical stimulus of 8 µm in 4 different TAFA4$^{GFP/+}$ neurons. The velocity of the mechanical probe was 800 µm/s during the forward motion of the mechanical stimulus. Holding potential: −100 mV. Right panel: frequency distribution of rapidly adapting (RA), slowly adapting (SA), ultra-slowly adapting (uSA) and mixed MA currents. Data collected over 33 TAFA4$^{GFP/+}$ neurons and stimulated with a standard mechanical stimulus of 8 µm.

(G) Velocity-related firing property of a TAFA4$^{GFP/+}$ neuron. Note that firing was enhanced as mechanical stimuli were applied with slow rates of onset (n=7).

Figure 3:
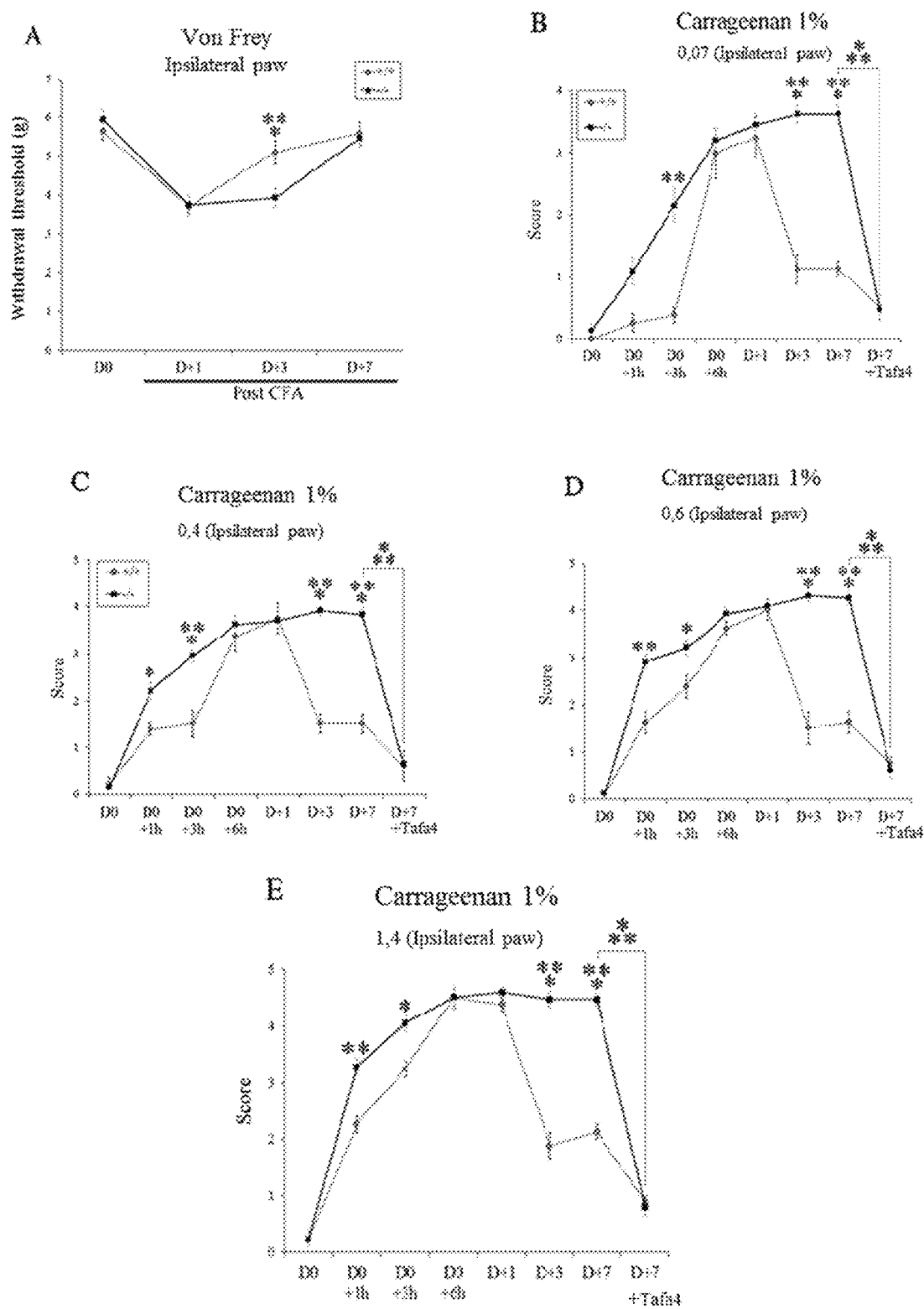
Figure 3:
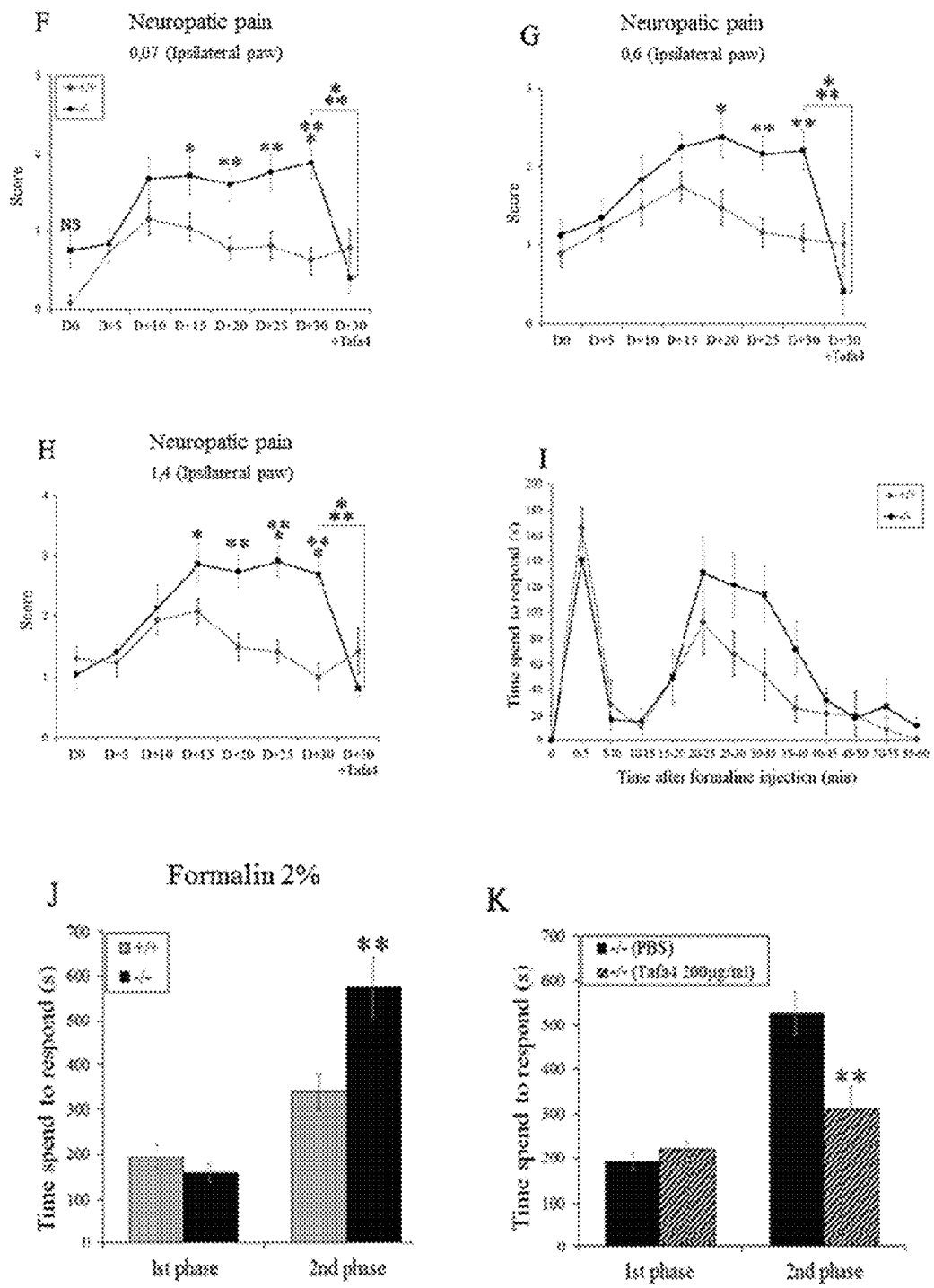

FIG. 3: Tissue injury-induced hypersensitivity is increased in TAFA4-null mice.

(A) Mechanical threshold of TAFA4-null mice (n=12) and WT littermates (n=11) using dynamic Von Frey apparatus, before and after CFA injection.

(B-E) Time course of mechanical sensitivity of TAFA4-null mice (n=12) and WT littermates (n=7) before (Day0) and following carrageenan injection using 4 different filaments of increasing calibers (0.07, 0.4, 0.6 and 1.4 g). At D+7, the score is before and 15 minutes after intrathecal injection of 2 µg of human recombinant TAFA4.

(F-H) Time course of mechanical sensitivity following sciatic nerve constriction (CCI) of TAFA4-null mice (n=12) and WT littermates (n=13) using 3 different filaments of increasing calibers (0.07, 0.6 and 1.4 g, n=15). Measures were determined before (Day0) and every 5 days after the CCI. At D+30, the score is before and 15 minutes after intrathecal injection of 2 µg of human recombinant TAFA4 (TAFA4-null mice (n=5), WT (n=7)).

(I, J) Time course and total time (in 2 phases: first 0-10 min and second 10-60 min) spent in flinching, biting and licking behavior following 2% formalin injection (WT n=11 and TAFA4-null mice n=12).

(K) Intrathecal injection of 2 µg of human recombinant TAFA4 restores formalin-evoked hypersensitivity to WT levels in TAFA4-null mice (Vehicle n=8, hTAFA4 n=8). Data shown are mean±SEM. *p<0.05, p<0.01, *p<0.001 one-way ANOVA followed by unpaired t-test.

Figure 4:
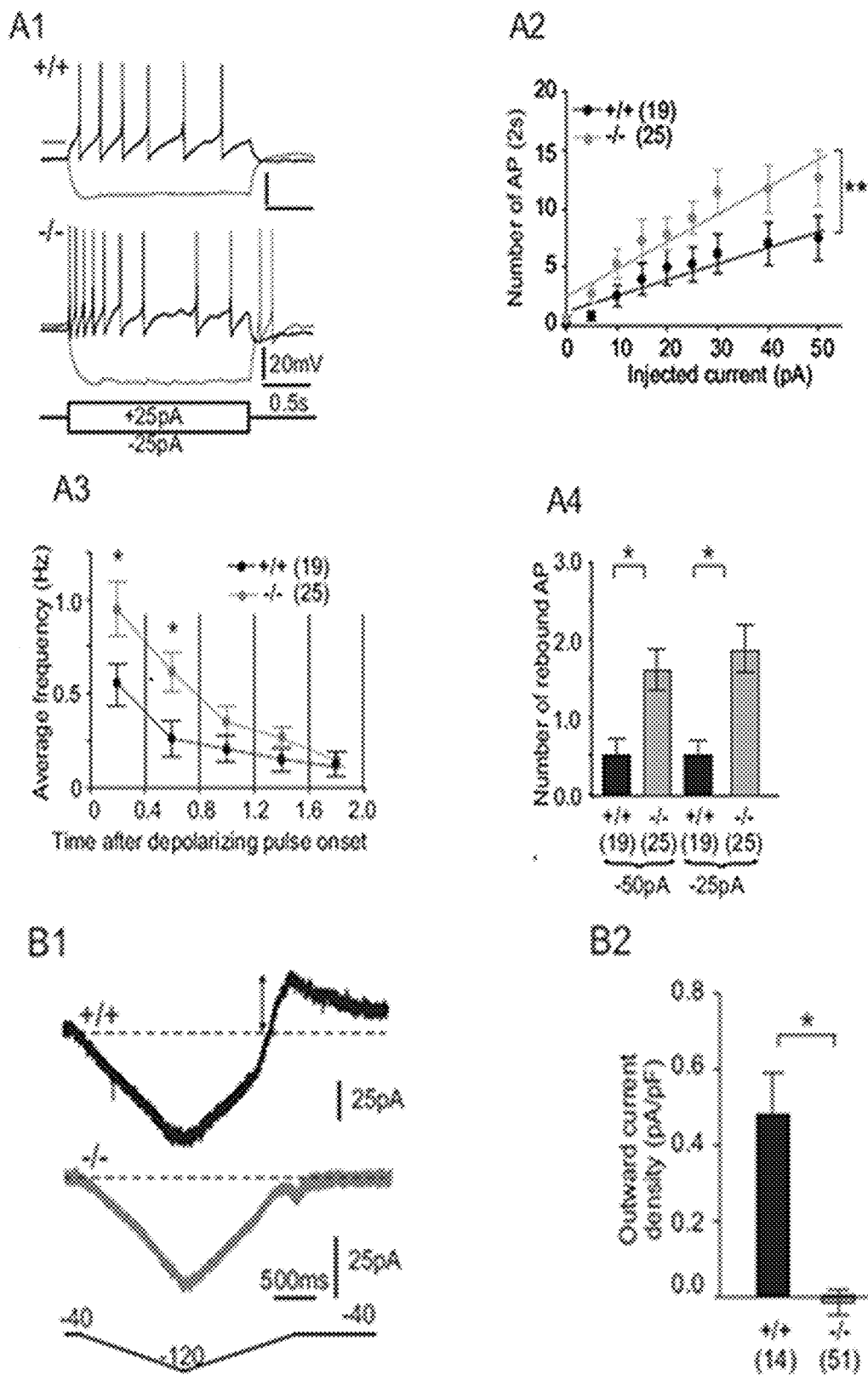
Figure 4:
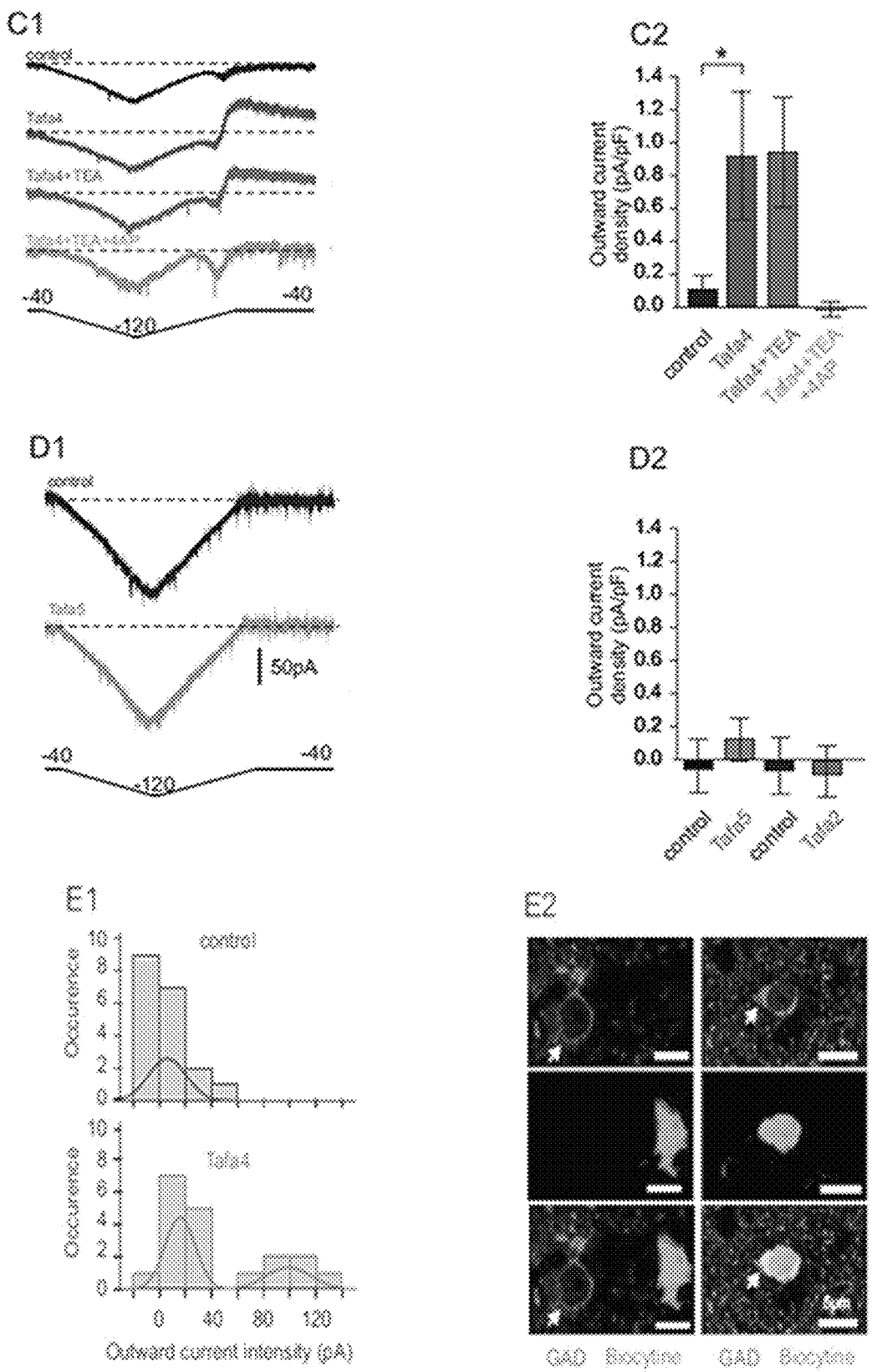

FIG. 4: Lamina IIi neuron excitability in TAFA4-null mice.

(A1) Representative recordings showing the responses of neurons from WT (top) or TAFA4-null (bottom) spinal slices to a 2 s depolarizing (+25) or hyperpolarizing (−25 pA) current pulse.

(A2) Quantification of the average number of AP elicited by current pulses of increasing intensities (5 to 50 pA). (ANCOVA, p<0.01).

(A3) Average firing rate at different times of the discharge elicited by a 2 s depolarizing current pulse (+25 pA) in lamina IIi neurons of WT and TAFA4-null mice.

(A4) Average number of rebound action potentials following a 2 s hyperpolarizing current pulse (−50 and −25 pA). (t-test, p<0.05.)

(B1) Representative current responses from WT and TAFA4-null neurons to a back and forth voltage ramp from −40 to −100 mV. Each trace represents the average of 5 consecutive responses. (B2) Quantification of the peak of the outward current measured at the end of the rising voltage ramp in lamina IIi neurons of WT and TAFA4-null animals (t-test, p<0.05).

(C1) Response of a TAFA4-null lamina IIi neuron to a back and forth voltage ramp in WT conditions, and in the presence of 20 nM recombinant TAFA4, TEA (2.5 mM), and 4AP (1 mM).

(C2) Quantification of the outward current measured at the end of the rising edge of the voltage ramp in TAFA4-Lamina IIi neurons. Notice the increase in outward current following TAFA4 application (p<0.05), and the blockade of this current by 4AP.

(D1, D2) Representative traces and quantification of the outward current in lamina Iii neurons of TAFA4-null animals following the bath superfusion of TAFA5 and TAFA2 (20 nM each).

(E1) Occurrence of low threshold outward current in WT and following recombinant TAFA4 superfusion.

(E2) Examples of lamina GAD65/67 negative (left) and positive (right) neurons. Images are single confocal planes. White arrows indicate the labeling of GAD-positive soma.

Figure 5:
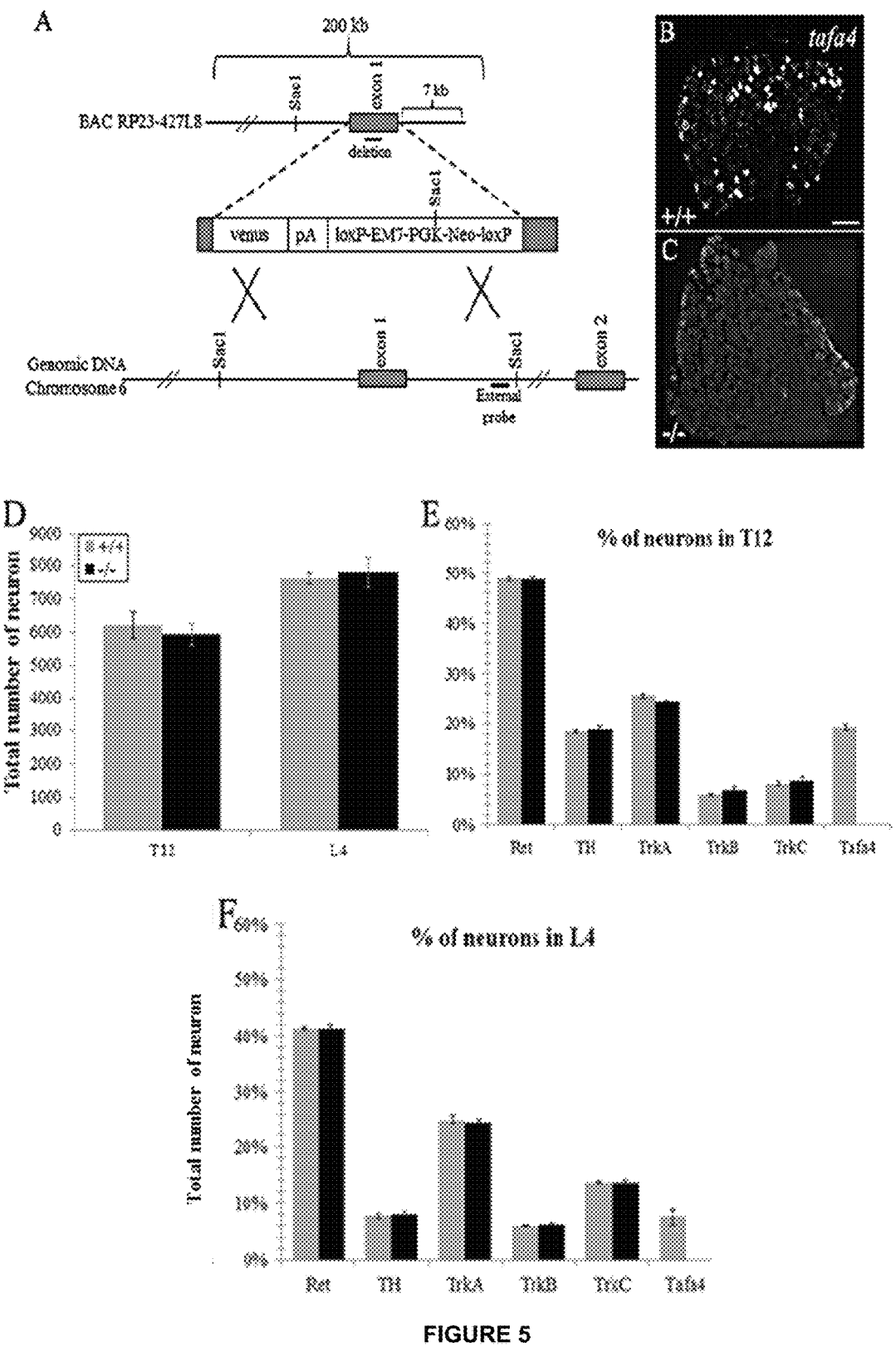
Figure 5:
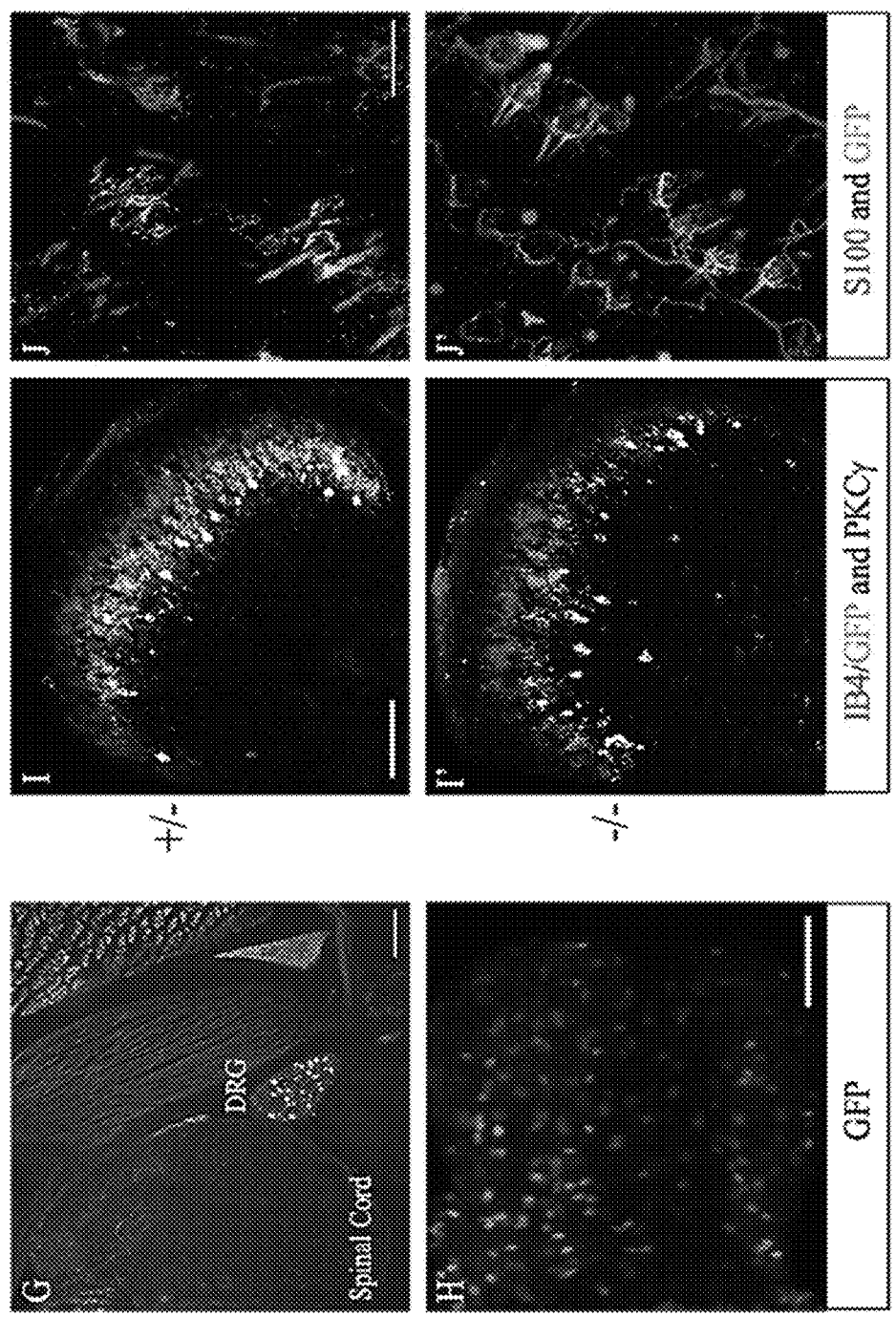

FIG. 5: Generation and presentation of TAFA4 GFP mice.

(A) Schematic representation of TAFA4GFP BAC-based strategy used to trigger homologous recombination in Tafa4 locus for the generation of TAFA4 knock-in mice.

(B-C) In situ hybridization with Tafa4 probe on adult thoracic DRG sections from WT (B) and TAFA4-null mice (C) (n=5).

(D) Total number of neuronal counts in WT DRG (n=3, 6209+/−385 in T12 and 7616+/−173 in L4) and TAFA4-null mice (n=3, 5933+/−324 in T12 and 7805+/−439 in L4).

(E, F) Percentage of Ret, TH, TrkA, TrkB, TrkC and TAFA4-positive neurons in T12 (B) and L4 (C) DRG of WT and TAFA4-null adult mice (n=3).

(G, H) Immunostaining of GFP on transversal section of newborn TAFA4$^{GFP/+}$ (G) and on whole mount adult DRG (H).

(I, I') Immunostaining of GFP and PKCγ with IB4 staining on lumbar spinal cord sections from adult TAFA4$^{GFP/+}$ mice (I) and TAFA4-null mice (I') (n>3).

(J, J') Immunostaining of GFP and S100 on back skin sections of TAFA4$^{GFP/+}$ (J) or TAFA4-null adult mice (J') (n>3).

Scale bars=100 µm. P>0.1 one-way ANOVA followed by unpaired t-test. Error bars represent SEM.

Figure 6:
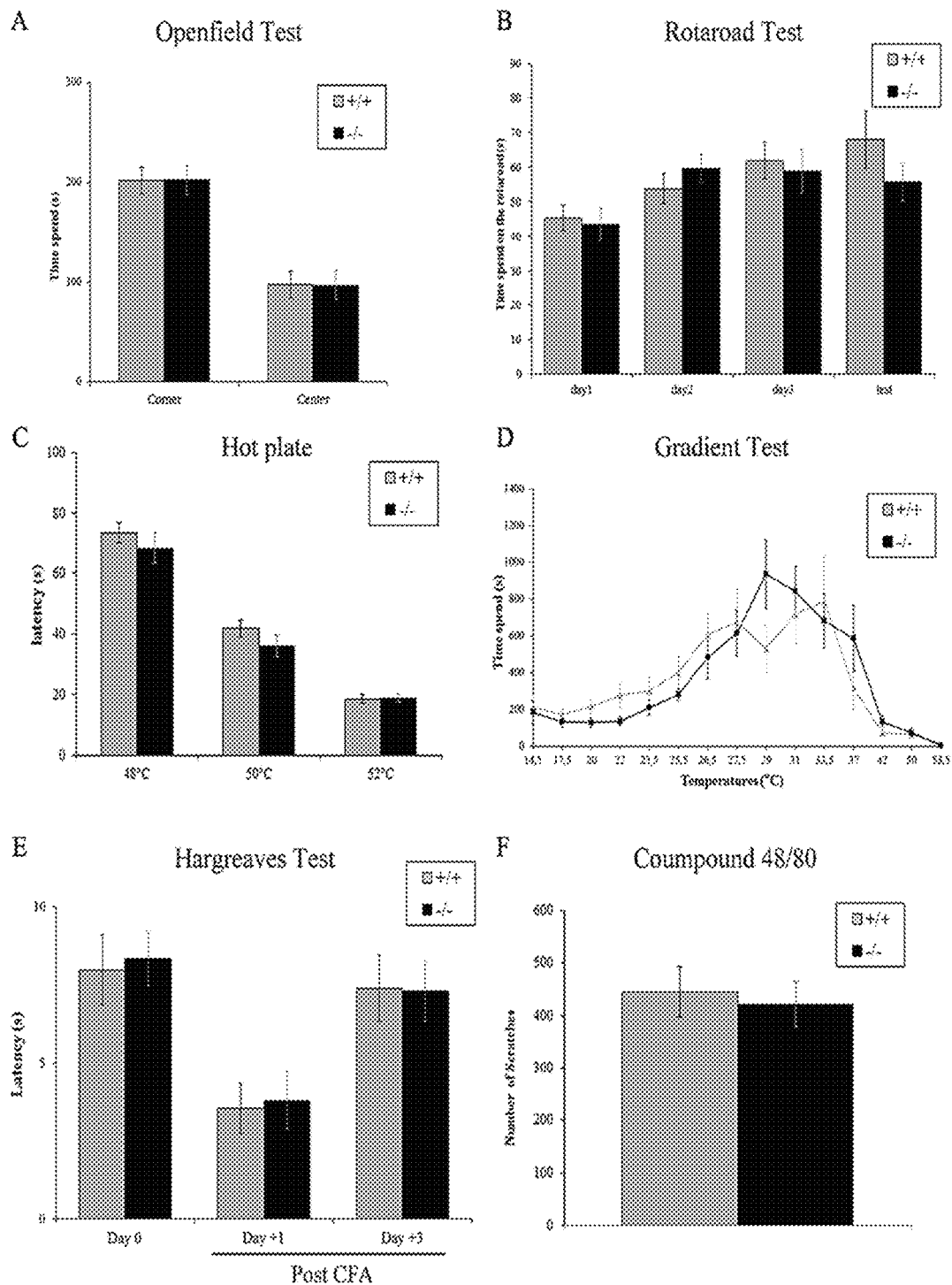

FIG. 6: TAFA4-null mice behave normally in terms of motor activity, anxiety, itch, and acute and injury-induced thermal hypersensitivity.

TAFA4-null mice display unaltered phenotype compared to WT littermate mice in anxiety with open field test (n=14 WT, n=17 TAFA4-null) (A), in motor coordination with rotaroad test (n=22 WT, n=21 TAFA4-null) (B), in hot plate test (n=18 WT, n=17 TAFA4-null) (C), in acute thermal sensitivity with gradient test (n=15 WT, n=17 TAFA4-null) (D), in CFA-induced thermal hyperalgesia (n=12 WT, n=14 TAFA4-null) (E) and in itch test after injection of 100 µg of the pruritogenic agent 48/80 (F). P>0.1 one-way ANOVA followed by unpaired t test. Error bars represent SEM.

Figure 7:
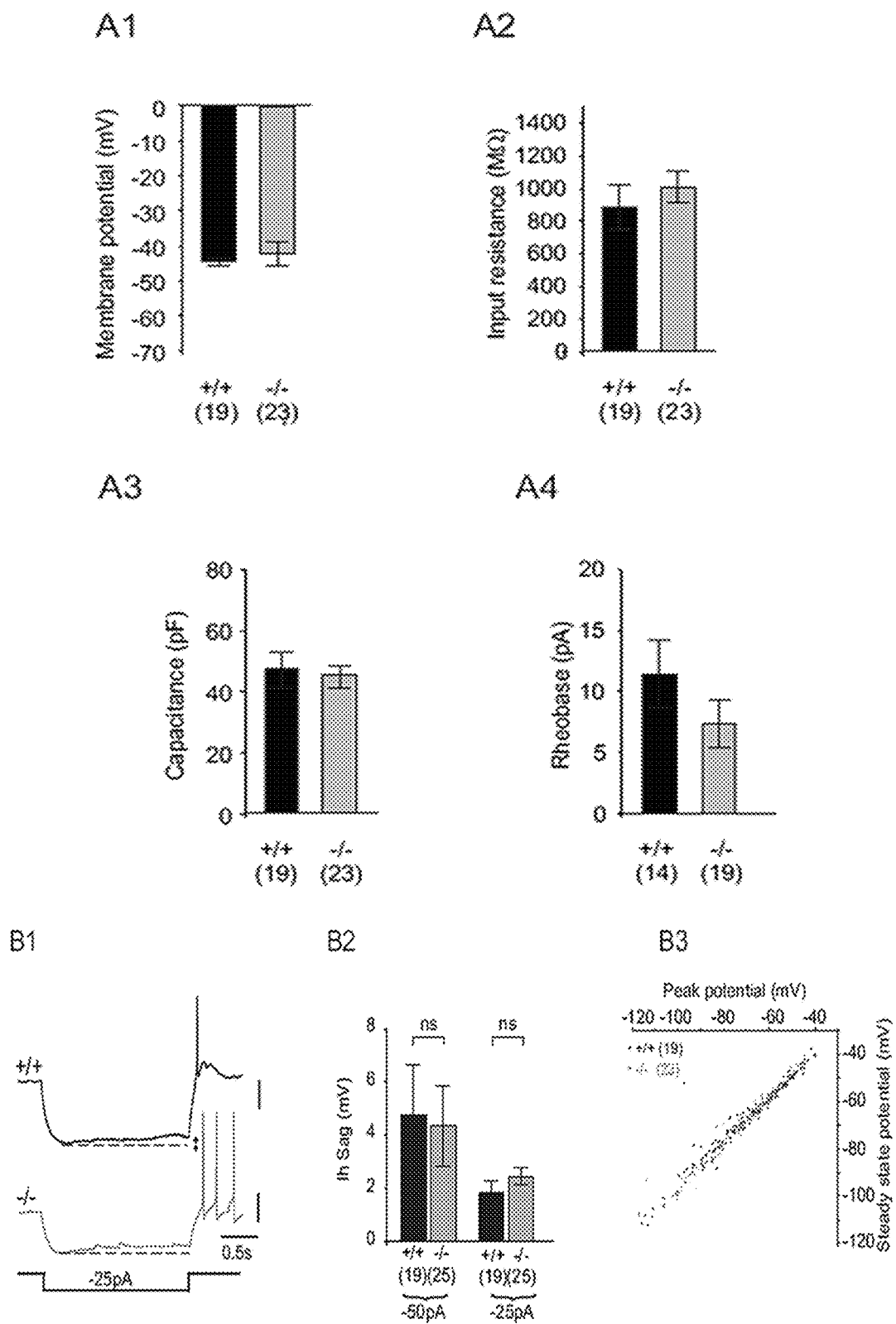
Figure 7:
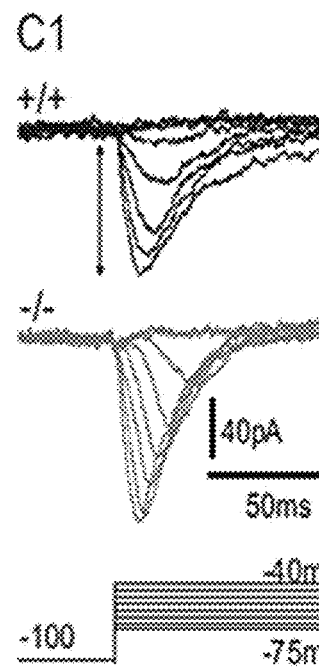
Figure 7:
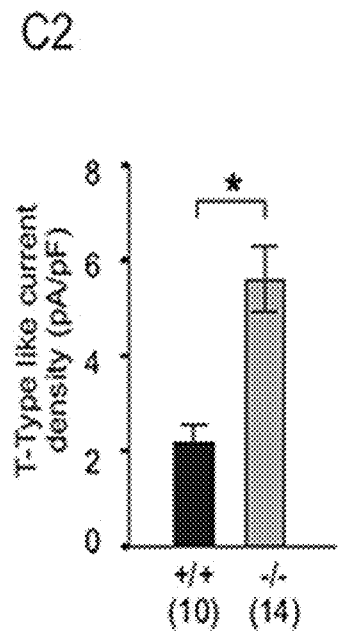
Figure 7:
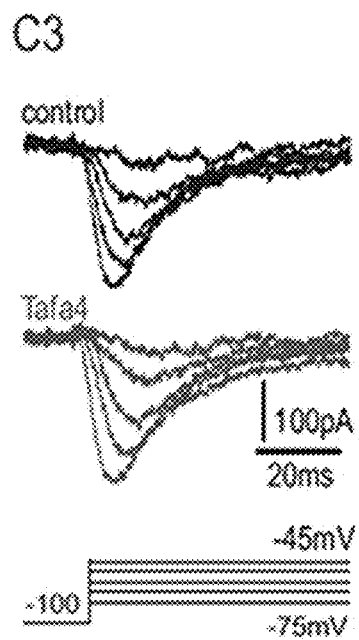
Figure 7:
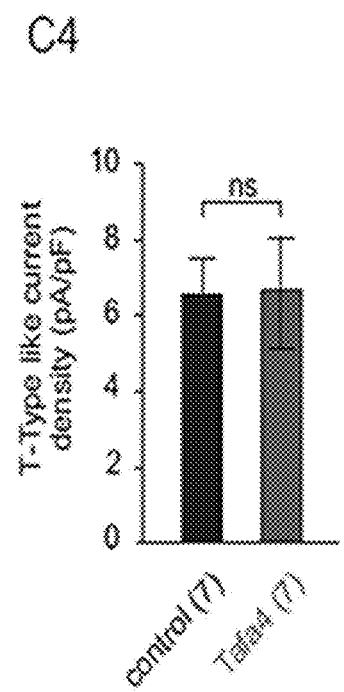

FIG. 7: Passive properties and low threshold cationic currents in TAFA4-null lamina IIi neurons.

(A) Average values of membrane potential (A1), cell input resistance (A2), cell capacitance (A3) and rheobase (A4) in lamina IIi neurons of WT and TAFA4-null animals.

(B1) Representative recordings showing the Ih sag evoked by a −25 pA hyperpolarizing current pulse in WT and TAFA4-null animals.

(B2) Quantification of the average Ih sag evoked by −50 and −25 pA hyperpolarizing current pulses. (B3) Relation between peak and steady-state potentials during a hyperpolarizing pulse (range −5 pA −50 pA) in lamina Iii neurons of WT and TAFA4-null animals.

(C1) Representative isolated T-type-like current responses of WT and TAFA4-null lamina IIi neurons evoked by depolarizing voltage steps of increasing amplitude (25 to 60 mV) from a holding potential of −100 mV.

(C2) Quantification of T-type-like current densities revealed significant differences between WT and TAFA4-null mice (t-test; p<0.05).

(C3, C4) T-type currents measured in TAFA4-null neurons before and after bath application of human recombinant TAFA4.

Figure 8:
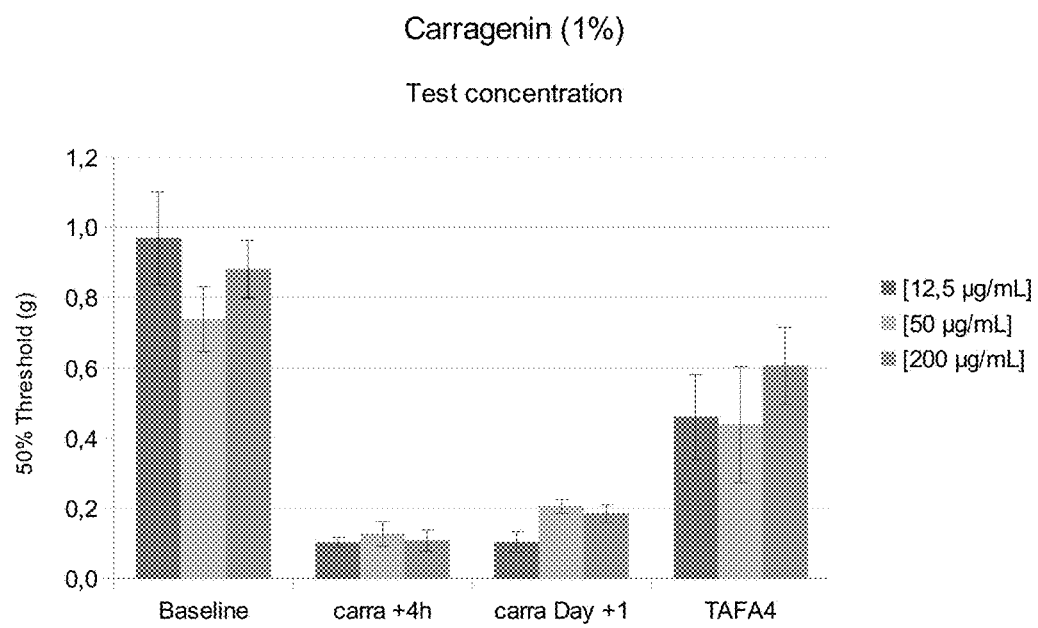

FIG. 8: Analgesic effect of intrathecal TAFA4 protein in vivo in a carrageenan model of pain.

Figure 9:
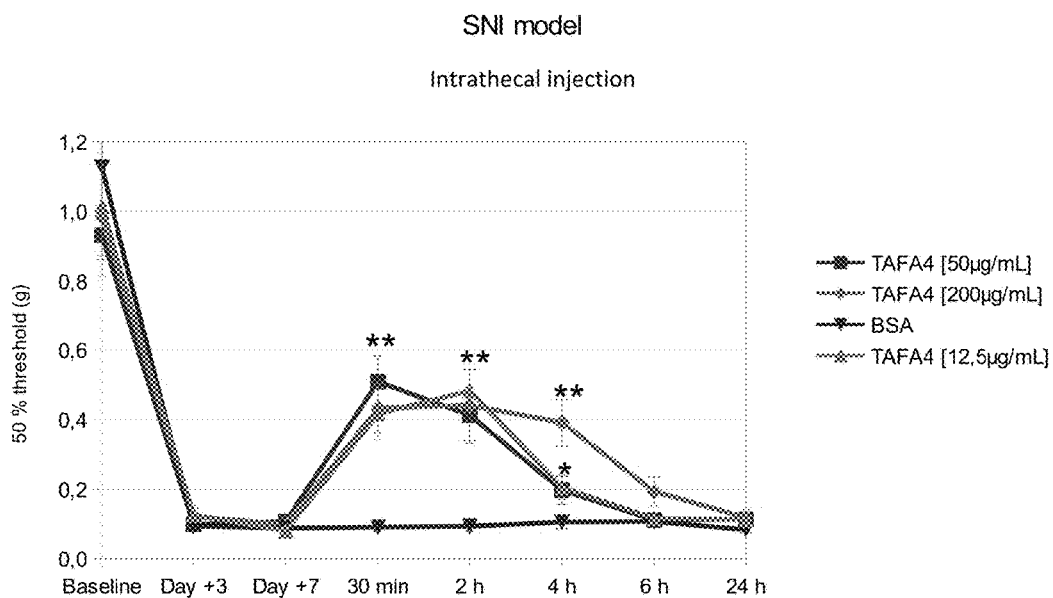

FIG. 9: Analgesic effect of intrathecal TAFA4 protein in vivo in an SNI model of neuropathic pain.

Figure 10:
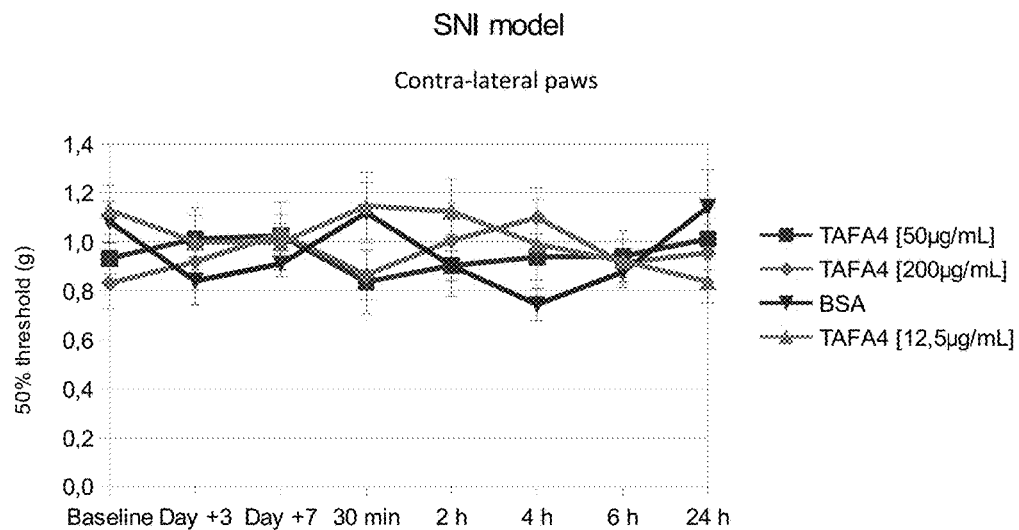

FIG. 10: Response of contra-lateral paws following intrathecal injection of TAFA4.

Figure 11:
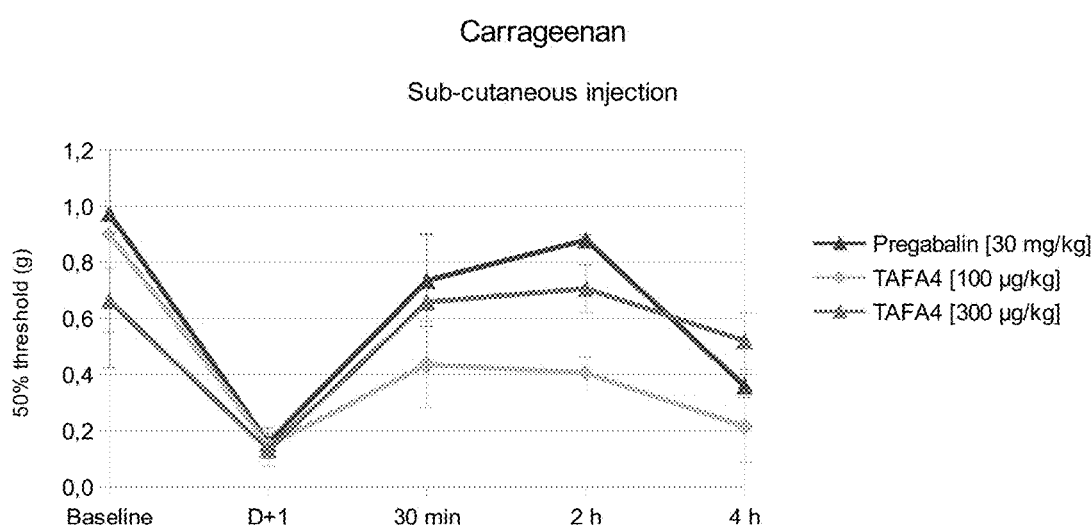

FIG. 11: Analgesic effect of subcutaneous TAFA4 protein in vivo in a carrageenan model of pain.

Figure 12:
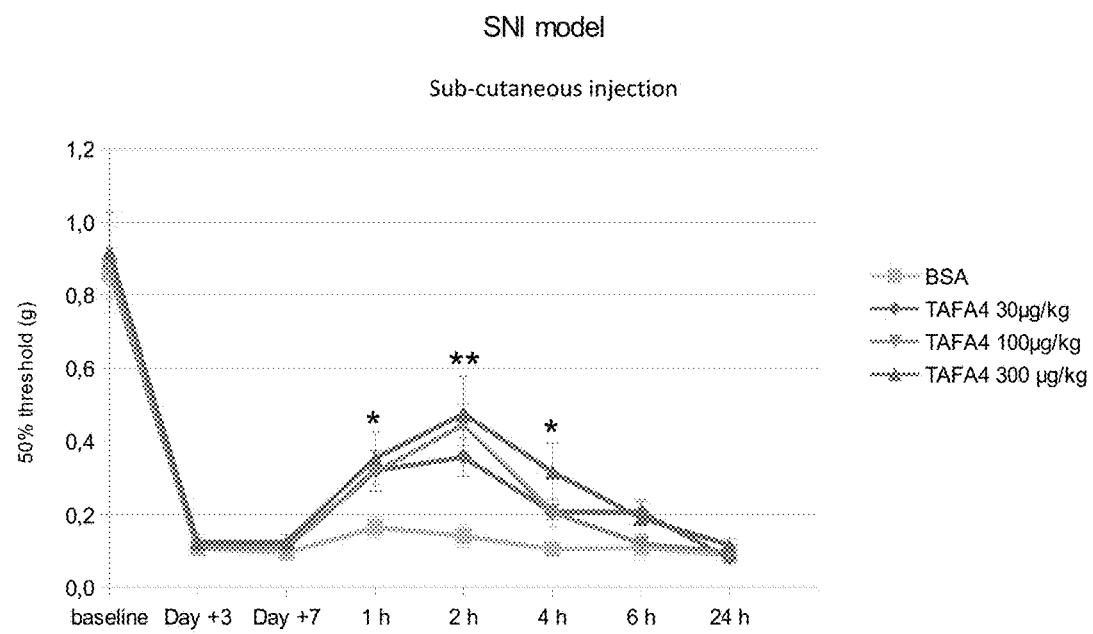

FIG. 12: Analgesic effect of subcutaneous TAFA4 protein in vivo in an SNI model of neuropathic pain.

Figure 13:
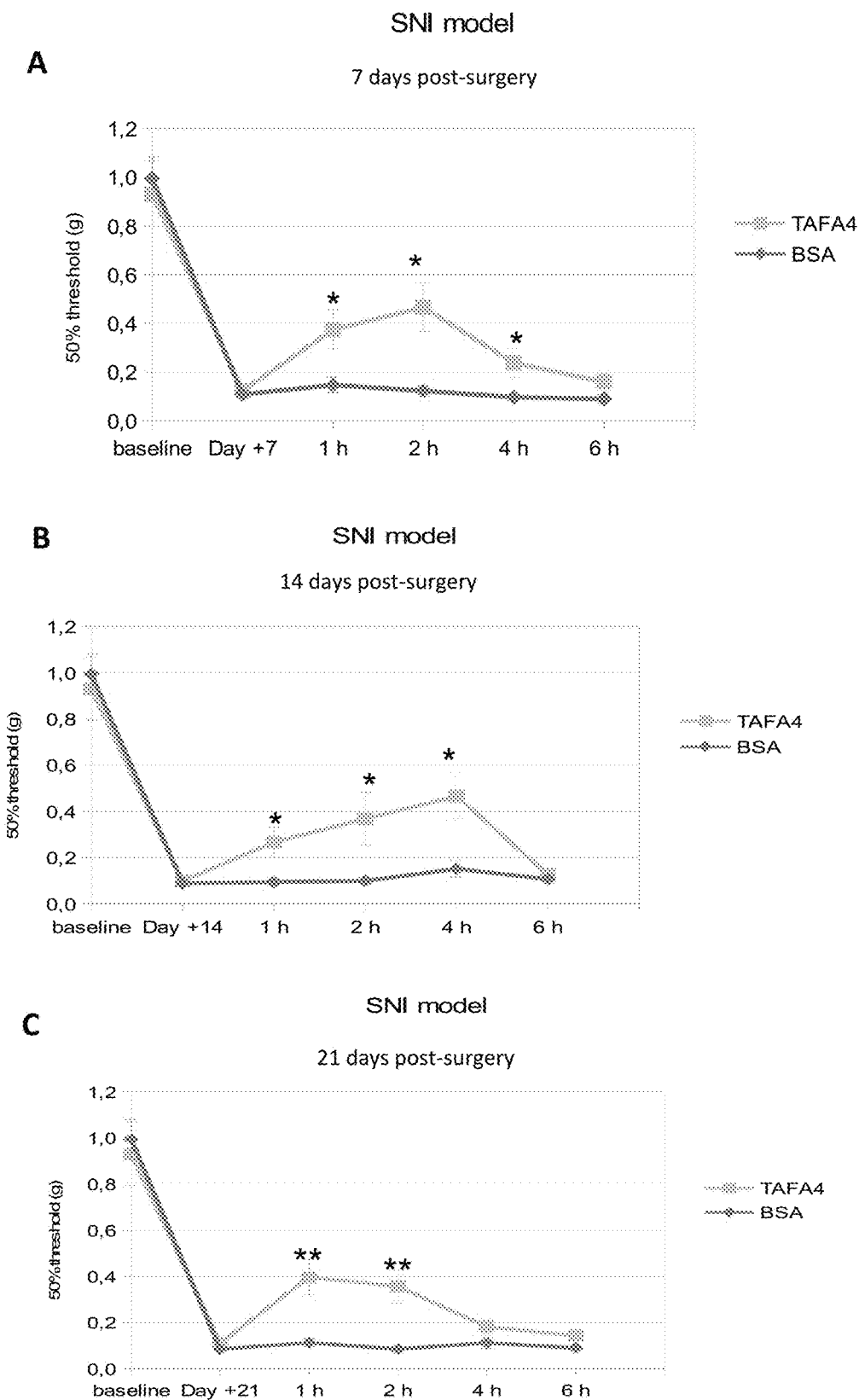

FIG. 13: Analgesic effect of subcutaneous TAFA4 protein in vivo in an SNI model of neuropathic pain 7 (FIG. 13A), 14 (FIG. 13B), and 21 (FIG. 13C) days post-surgery.

Figure 14:
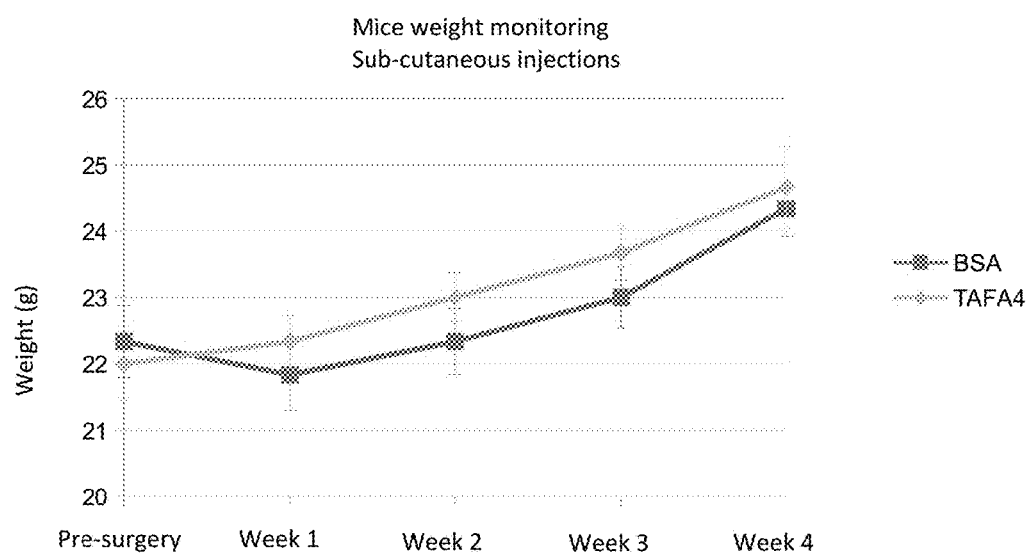

FIG. 14: Weight monitoring.

DETAILED DESCRIPTION OF THE INVENTION

The present invention provides new therapeutic approaches for treating pain. More particularly, the invention provides a new solution to efficiently manage pain, in particular neuropathic pain and inflammatory pain. This solution involves a modulation of sensory sensitivity and/or neuronal excitability by using a TAFA4 compound.

TAFA4 is a small secreted protein belonging to the family of TAFA chemokine-like proteins discovered very recently (Tang et al., 2004). TAFA4 is synthesized as a 140 amino acid precursor that contains a 35 amino acid signal sequence and a 105 amino acid mature chain. Human TAFA4 has 90% amino acid identity with mouse TAFA4. Real-time PCR analysis indicates that TAFA4 mRNA expression is restricted to the central nervous system (CNS), with the highest level in the thalamus.

WO 2006/013462 relates to several gene sequences and uses thereof. However, the proposed uses of these genes, particularly NsG28, are essentially speculative and based merely on expression profiles. In this regard, while the reference mentions pain, there is no rationale for said use and no experimental data to support any such activity which, at least for some of these genes, turns out to be erroneous. Furthermore, the reference does not disclose the effect or use of isolated proteins, so that a skilled artisan would not consider this document as providing any technical teaching.

Before the present invention, the biological functions of TAFA family members remained to be determined.

The inventors have now surprisingly demonstrated, for the first time, that TAFA4 protein is involved in the control of pain. More particularly, the invention shows that TAFA4 is specifically expressed in a particular subset of dorsal root ganglia (DRG) neurons called C-LTMRs (C-fibers low threshold mechanoreceptors). The invention further shows that TAFA4-null mice present sustained mechanical and chemical hypersensitivity following tissue injury, both of which can be reversed by administration of a human recombinant TAFA4 protein.

The inventors have also demonstrated that TAFA4-null mice present significant hyperexcitability of inner lamina II spinal cord neurons. Without being bound by theory, the inventors believe that, in response to painful stimuli, under pathological conditions, elevated neuronal activity in C-LTMRs enhances the secretion of TAFA4 protein that modulates the excitability of specific interneurons of the spinal cord through the activation of a low threshold current.

Interestingly, the inventors have also demonstrated, in the experimental part, that TAFA4 protein can specifically target mechanically and chemically induced nociceptive signals, without targeting temperature-induced signals. This is a considerable advantage in comparison to known pain-treating products which are less specific since they also target thermo-induced nociception.

TAFA4 compounds and compositions of the invention are capable of activating a new analgesic pathway by modulating C-LTMR-nociceptor-mediated excitability of spinal cord interneurons (preferably lamina Iii interneurons), for example, via modulation of the activity of receptors present on said interneurons (such as potassium ion channels, calcium ion channels or low density lipoprotein receptors, e.g., LRP1).

The invention will be best understood by reference to the following definitions:

Definitions

Within the context of the present invention, the term "TAFA4 compound" designates a TAFA4 protein or a TAFA4 agonist as defined below.

As used herein, the term "TAFA4 protein" designates a protein belonging to the family of TAFA chemokine-like proteins, preferably comprising the amino acid sequence of SEQ ID NO: 1 (which corresponds to the human TAFA4 amino acid sequence) or SEQ ID NO: 2 (which corresponds to the mouse TAFA4 amino acid sequence), and any natural variant thereof (e.g., variants present in other animal species, or variants as a result of polymorphism or splicing). Within the context of the present invention, the term "TAFA4 protein" also includes any protein comprising a sequence having at least 90% sequence identity to the sequence shown in SEQ ID NO: 1 or 2, preferably at least 95% sequence identity or more. Typically, a TAFA4 protein is able to modulate nociceptor sensitivity and/or neuronal excitability, as defined below.

Within the context of the present invention, the term "TAFA4 gene" designates a gene or nucleic acid that codes for a TAFA4 protein. In particular, a "TAFA4 gene" includes any nucleic acid encoding a protein comprising SEQ ID NO: 1 or 2, or a natural variant of such a protein.

The term "TAFA4 agonist", within the context of the present invention, encompasses any substance having, mediating or regulating TAFA4 activity (for example, a peptide, a polypeptide, a recombinant protein, a conjugate, a chemokine, an antigen, a natural or artificial ligand, a homolog, a nucleic acid, DNA, RNA, an aptamer, etc., or a combination thereof). In particular, TAFA4 agonists modulate the activity of a receptor involved in TAFA4 activity, for example by binding such a receptor, and thus modulating neuronal excitability. The term "agonist" encompasses both full and partial agonists. Typically, "TAFA4 agonist" designates any compound that can modulate sensitivity of sensory neurons (preferably C-LTMRs) and/or excitability of interneurons (preferably spinal cord Iii interneurons), in particular by modulation of the activity of receptors present on said neurons, as described in the present application.

"TAFA4 agonist" encompasses any peptide fragment of a TAFA4 protein that modulates excitability of nociceptors or interneurons, preferably of C-fiber nociceptors (preferably C-LTMRs) or spinal cord interneurons (preferably spinal cord lamina Iii interneurons). Typically, a TAFA4 agonist is a peptide comprising a fragment of less than 60 amino acid residues of SEQ ID NO: 1 or 2. Preferably, a TAFA4 agonist comprises at least 10 consecutive amino acid residues of SEQ ID NO: 1 or 2, preferably of at least 20, 15, 25, 27, 28 or 30 consecutive amino acid residues. In the most preferable embodiment, such a fragment is a fragment comprising at least 10, 15, 20, 25, 27, 28 or 30 consecutive amino acid residues of the N-terminal part of a "TAFA4 protein" as defined above. In another embodiment, a TAFA4 agonist comprises at least 10, 15, 20, 25, 27, 28 or 30 consecutive amino acid residues of the C-terminal part of a "TAFA4 protein" as defined above. Specific examples of a TAFA4 agonist are: (i) a peptide comprising the amino acid sequence of SEQ ID NO: 3 (which corresponds to 25 amino acid residues of the N-terminal part of the human TAFA protein of SEQ ID NO: 1); and (ii) a peptide comprising the amino acid sequence of SEQ ID NO: 4 (which corresponds to 27 amino acid residues of the C-terminal part of the human TAFA protein of SEQ ID NO: 1). A TAFA4 agonist of the invention is able to modulate nociceptor sensitivity and neuronal excitability, as in the present application. The term "sequence identity" as applied to nucleic acid or protein sequences refers to the quantification (usually as a percentage) of nucleotide or amino acid residue matches between at least two sequences aligned using a standardized algorithm such as Smith-Waterman alignment (Smith and Waterman (1981) J Mol Biol 147:195-197), CLUSTALW (Thompson et al. (1994) Nucleic Acids Res 22:4673-4680), or BLAST2 (Altschul et al. (1997) Nucleic Acids Res 25:3389-3402). BLAST2 may be used in a standardized and reproducible way to insert gaps in one of the sequences in order to optimize alignment and to achieve a more meaningful comparison between them.

The term "pain", within the context of the present invention, refers to any pain or sensitivity associated with tissue damage. Preferably, the term "pain" as used herein is understood as an abnormal sensitivity, i.e., typically as a hypersensitivity which is mediated by nociceptors (in particular by C-LTMRs). The term "pain" includes any pain selected from a nociceptor-mediated pain (also called herein a nociceptive pain), a neuropathic pain, an inflammatory pain, a pathological pain, an acute pain, a subacute pain, a chronic pain, a mechanical pain, a chemical pain, a somatic pain, a visceral pain, a deep somatic pain, a superficial somatic pain, a somatoform pain, allodynia, hyperalgesia, or a pain associated with a nerve injury. "Nociceptive" pain or "nociceptor-mediated" pain occurs in response to the activation of a specific subset of peripheral sensory neurons (nociceptors) by intense or noxious stimuli. Nociceptive pain according to the invention includes mechanical pain (crushing, tearing, etc.) and chemical pain (iodine in a cut, chili powder in the eyes). Examples of nociceptive pain include but are not limited to traumatic or surgical pain, labor pain, sprains, bone fractures, burns, bumps, bruises, injections, dental procedures, skin biopsies, and obstructions. Nociceptive pain includes visceral pain, deep somatic pain and superficial somatic pain. Visceral pain is diffuse, difficult to locate and often referred to a distant, usually superficial, structure. It may be accompanied by nausea and vomiting and may be described as sickening, deep, squeezing, and dull. Deep somatic pain is initiated by stimulation of nociceptors in ligaments, tendons, bones, blood vessels, fasciae and muscles, and is dull, aching, poorly localized pain. Examples of deep somatic pain include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns. Inflammatory pain is pain that occurs in the presence of tissue damage or inflammation including post-operative pain, post-traumatic pain, arthritic (rheumatoid or osteoarthritis) pain and pain associated with damage to joints, muscles, and tendons as in axial low back pain. Inflammation is responsible for the sensitization of peripheral sensory neurons, leading to spontaneous pain and invalidating pain hypersensitivity. Acute or chronic pathological tissue inflammation strongly impacts pain perception by sensitizing peripheral sensory neurons, giving rise to local and incapacitating pain hypersensitivity. Inflammatory mediators are known to enhance nociceptive primary afferent fiber excitability, in part by modifying the expression and/or function of ion channels present in nerve endings. Neuropathic pain is a common type of chronic, non-malignant pain, which is the result of an injury or malfunction in the peripheral or central nervous system. Neuropathic pain may have different etiologies, and may occur, for example, due to trauma, surgery, herniation of an intervertebral disk, spinal cord injury, diabetes, infection with herpes zoster (shingles), HIV/AIDS, late-stage cancer, amputation (including mastectomy), carpal tunnel syndrome, chronic alcohol use, exposure to radiation, and as an unintended side effect of neurotoxic treatment agents, such as certain anti-HIV and chemotherapeutic drugs. It is often characterized by chronic allodynia (defined as pain resulting from a stimulus that does not ordinarily elicit a painful response, such as light touch) and hyperalgesia (defined as an increased sensitivity to a normally painful stimulus), and may persist for months or years beyond the apparent healing of any damaged tissues. Pain may also occur in patients with cancer, which may be due to multiple causes: inflammation, compression, invasion, or metastatic spread into bone or other tissues. Pain also includes migraine and headaches associated with the activation of sensory fibers innervating the meninges of the brain. Preferably, TAFA4 compounds of the invention are used for preventing or treating a neuropathic and/or inflammatory pain.

"Threshold" of pain, within the context of the present invention, designates the minimum stimulus necessary to produce pain. In particular, the pain perception threshold is the point at which the stimulus begins to hurt, and the pain tolerance threshold is reached when the subject acts to stop the pain. For example, pain thresholds are measured by gradually increasing the intensity of a stimulus such as electric current or heat applied to the body.

The term "nociceptors", within the context of the present invention, designates all possible sensory neurons that mediate nociceptive information relative to pain. Nociceptors innervate cutaneous tissues. The term "nociceptors" includes, without limitation, mechanoreceptors, mechano-nociceptors, multimodal nociceptors, chemoreceptors and/or pruriceptors that detect and transduce a variety of noxious stimuli, including chemical, thermal or mechanical stimuli or combinations of these stimuli. A specific example of nociceptors according to the invention correspond to the low-threshold mechano-receptor (C-LTMR), specifically responding to mechanical and chemical stimuli.

Nociceptors may be modulated by TAFA4 compounds of the invention, or may use such compounds to further modulate the excitability of specific interneurons of the spinal cord, for example, through the activation of a low threshold current.

The term "interneurons", within the context of the invention, designates relay neurons which transmit information between other neurons. Preferably, interneurons are neurons that relay nociceptive information from sensory neurons to spinal cord projection neurons. The preferred interneurons according to the invention are spinal cord lamina IIi interneurons. The interneurons are neurochemically diverse; for example, they can be excitatory interneurons (using glutamate) and/or inhibitory interneurons (using GABA or glycine).

Typically, interneurons according to the invention are interneurons that are directly and/or indirectly modulated by TAFA4 compounds as described in the present application. The interneurons express various histochemical markers and various types of receptors, including endocytic receptors, metabotropic receptors, inotropic receptors, growth factor receptors, as well as other signaling molecules, and interneuron excitability is preferably modulated via modulation of the activity of such receptors.

The term "receptor", within the context of the present invention, includes any receptor selected from metabotropic receptors, endocytic receptors (for example, LRP1 receptors) and ionotropic receptors such as ligand-gated ion channels and voltage-gated ion channels (for example, potassium channels, calcium channels and sodium channels), or a combination thereof, the activity of which can be modulated by TAFA4 compounds of the invention. Endocytic receptors include receptors that mediate the internalization of a variety of extracellular macromolecules and macromolecular complexes, including lipoproteins, proteinases, proteinase-inhibitor complexes and extracellular matrix proteins. A specific example of such endocytic receptor of the invention is the low-density lipoprotein receptor-related protein 1 (LRP1 receptor). Endocytic receptors include receptors that are also involved in ligand-mediated signal transduction. Ionotropic receptors include ion channels, channel-linked receptors and ligand-gated ion channels (LGICs). Voltage-gated ion channels (such as potassium channels, sodium channels, and calcium channels) are channels playing a fundamental role in neuronal excitability which are directly responsible for initiation and propagation of action potentials, and implicated in different chronic pain disorders. LGICs include a group of transmembrane ion channels that are opened or closed in response to the binding of a chemical messenger (i.e., a ligand), such as a neurotransmitter. The binding site of endogenous ligands on LGIC protein complexes are normally located on a different portion of the protein (an allosteric binding site) compared to where the ion conduction pore is located. The direct link between ligand binding and opening or closing of the ion channel, which is characteristic of ligand-gated ion channels, is contrasted with the indirect function of metabotropic receptors, which use second messengers. LGICs are also different from voltage-gated ion channels (which open and close depending on membrane potential) and stretch-activated ion channels (which open and close depending on mechanical deformation of the cell membrane). Metabotropic receptors comprise a large protein family of transmembrane receptors that sense molecules outside the cell and activate inside signal transduction pathways and, ultimately, cellular responses. Metabotropic receptors include G protein-coupled receptors (GPCRs), also known as seven-transmembrane domain receptors, heptahelical receptors, serpentine receptors, and G protein-linked receptors (GPLR).

The term "modulation" or "modulation of neuronal excitability", within the context of the present invention, designates a change in sensitivity and/or excitability of neurons involved in transmission of pain signals by using TAFA4 compounds of the invention. The term "modulation" includes a "decrease" of neuronal excitability and/or an "increase" of neuronal excitability, depending on the type of interneurons the activity of which is modulated. Neurons which can be modulated by TAFA4 are sensory neurons and/or interneurons. Neurons may be modulated by TAFA4 directly or indirectly, electrically or chemically, via receptors or via ion channels, or by any combination of the above modulatory modes. An example of nociceptor modulation is a nociceptor modulation comprising a control of the threshold of somatic sensation in response to mechanical or chemical stimuli. An example of interneuron modulation is a modulation of interneuron excitability comprising a modulation of the activity of receptors present on spinal cord interneurons.

Within the context of the present invention, the term "treatment" or "treating" pain in a subject designates delaying, stabilizing, curing, healing, alleviating, relieving, altering, ameliorating, improving, remedying or affecting any form of pain in a subject as described herein, or any disease or condition associated with pain (in particular any neuropathic condition associated with neuropathic pain), or any symptom of such a disease or condition, after the application or administration of a suitable TAFA4 compound or composition according to the invention. The term "treatment" or "treating" also refers to any indicator of success in the treatment of pain (which may be associated with any injury, pathology or condition), including any objective or subjective parameter such as abatement, remission, slowing progression or severity, stabilization, diminishing of symptoms of pain, or making it more tolerable to the subject. The term "treating" pain also includes increasing pain tolerance and/or decreasing perceived pain. In particular embodiments, the methods, compounds and composition of the invention are for increasing pain tolerance and/or for decreasing perceived pain. As used herein, the term "pain tolerance" refers to the amount of pain that a subject can perceive and withstand before breaking down emotionally and/or physically. Pain tolerance is distinct from pain threshold (the minimum stimulus necessary to produce pain). As used herein, "increasing pain tolerance" generally refers to a situation where a subject can develop a greater pain tolerance (that is, less perceived pain) when compared to a previous state, for instance, following administration of suitable TAFA4 compounds or compositions to a subject.

Within the context of this invention, "preventing" or "prevention" in relation to pain in a subject refers to at least the reduction of likelihood of the risk of (or susceptibility to) acquiring any kind of pain by a subject, after the application or administration of a suitable TAFA4 compound or composition according to the invention. For example, "preventing" includes causing at least one of the clinical symptoms of pain not to develop in a subject that may be exposed to or predisposed to, but does not yet experience or display symptoms of pain.

Active Ingredient

An object of the present invention is a TAFA4 compound for use as an active ingredient for preventing or treating pain in a subject, in particular neuropathic pain, inflammatory pain, acute pain, sub-acute pain, chronic pain, allodynia, hyperalgesia, partially treated pain, chemically induced pain, and mechanically induced pain, as well as refractory pains, while preferably advantageously avoiding deleterious side effects. In a preferred embodiment, the TAFA4 compound is to efficiently manage neuropathic pain or inflammatory pain. The compounds according to the invention may also be used to prevent or treat chronic pain in subjects suffering from pathologies such as cancer, burns, etc., for which generally analgesics (such as morphine) may be administered for a long period, optionally in delayed form. The compounds according to the invention may also be used together with reduced daily doses of morphine in order to improve the clinical picture of patients (by limiting side effects of morphinomimetics, such as intestinal disorders, for example).

In a preferred embodiment, the compound of the invention is a TAFA4 protein comprising the sequence of SEQ ID NO: 1 or a sequence having at least 90% identity to SEQ ID NO: 1, or a TAFA4 agonist, preferably comprising a fragment of SEQ ID NO: 1, more preferably at least a 30aa fragment thereof as indicated in the sequence of SEQ ID NO: 2, that modulates the activity of at least one receptor present on spinal cord lamina IIi interneurons (in particular, the low density protein LRP1 receptor or a potassium channel, a calcium channel, or another physiologically relevant receptor). In a particular embodiment, the TAFA4 compounds of the invention advantageously modulate the activity of an additional receptor (distinct from the first receptor).

Subject

In the context of the present invention, the patient or subject is an animal, preferably a vertebrate, typically a mammal. In a preferred embodiment, the mammal is a human being of any age or sex. The mammal may further be an animal, in particular a domestic or breeding animal, in particular a horse, a dog, a cat, etc. In a particular embodiment, the subject suffers from a neuropathic pain or an inflammatory pain, in particular a chronic inflammatory pain. In another particular embodiment, the subject is afflicted with any disease or condition associated with pain, initiated in any manner.

Compositions

The invention also relates to a pharmaceutical composition comprising a TAFA4 compound as herein described as an active ingredient, and preferably a pharmaceutically acceptable carrier.

A "pharmaceutical composition" refers to a formulation of a compound of the invention (active ingredient) and a medium generally accepted in the art for the delivery of biologically active compounds to a subject in need thereof. Such carriers include all pharmaceutically acceptable carriers, diluents, media or supports therefore. This carrier can be selected for example from methyl-beta-cyclodextrin, a polymer of acrylic acid (such as carbopol), a mixture of polyethylene glycol and polypropylene glycol, monoethanolamine and hydroxymethylcellulose. Conventional pharmaceutical practice may be employed to provide suitable formulations or compositions to subjects, for example in unit dosage form.

This composition is typically a local analgesic/anti-hyperalgesic composition.

The compounds and compositions of the invention are adapted for use for preventing, alleviating or treating pain in a subject as described above.

The composition of the invention can further comprise at least one additional active compound. This compound can be advantageously selected from a SAID, NSAID or opioid drug.

In another embodiment, a compound or composition of the invention can also be administered, for example, along with an agent intended to treat a coincident condition (e.g., an antitumor agent).

The compounds for use in the present invention may be administered simultaneously, separately or sequentially.

Methods of Production of Compounds of the Invention

The present invention also concerns methods of production of TAFA compounds.

TAFA4 compounds of the invention (e.g., protein or peptide agonists) can be produced by any conventionally known protein expression method and purification method, for example: (i) a method for synthesizing peptides; (ii) a method for purifying and isolating them from the living body or cultured cells; or (iii) a method for producing them with the use of genetic recombination techniques, and the like (for example, the standard techniques described for example in Molecular Cloning (Sambrook, J., Fritsch, E. F., Maniatis, T., Cold Spring Harbor Laboratory Press) (1989) and Current Protocols in Molecular Biology (Ausubel, F. M., John Wiley and Sons, Inc. (1989)). Preferred proteins or agonists for use in the invention are therefore isolated or purified. As commonly used, "isolated" indicates for instance that the protein or agonist is at least separated from some components of its natural or production environment such as a cell culture medium or living organism. More preferably, the proteins or agonists are used as isolated or pure material with a purity level above 50%, above 60%, above 70%, above 80%, above 90%, or even more preferably above 95%. The isolated or purified protein or agonist may then be combined or mixed with additional ingredients such as excipients or further active agents, as described in subsequent sections.

Treatment/Protocol/Regimen

Also taught herein is a method for the prevention or treatment of pain in a subject. An aim of the method is modulating neuronal excitability using TAFA4 compounds or compositions as defined above. A particular method for preventing, alleviating or treating a nociceptor-mediated pain (in particular a C-LTMR-mediated pain) in a subject in need thereof comprises administering to the subject an effective amount of a TAFA4 compound or composition as herein described.

A further particular method for preventing, alleviating or treating pain in a subject in need thereof comprises a step of administering to said subject a TAFA4 compound or composition, as herein described, in a therapeutically effective amount, possibly in combination with at least one additional active compound such as any one of the molecules mentioned in the background part, for example aspirin, ibuprofen, paracetamol, opioid, etc.

Preferably, the treatment method refers to treating neuropathic pain or neuropathy, comprising any improvement in the symptoms of such a neuropathy or any retardation or reduction of outward signs, for example a reduction of their frequency, of the trouble or discomfort, of pain, or even total disappearance of the neuropathy. In a particular embodiment, the TAFA4 compounds or compositions of the invention are useful in preventing neuropathic pain or preventing neuropathy before development of the first signs of the disease in order to protect a subject from such a neuropathic pain or neuropathy to which the subject is, or may be, exposed.

The duration, dosages and frequency of administering compounds or compositions of the invention for such a treatment may be also adapted according to different forms of pain (i.e., acute or chronic neuropathic pain). The treatment may be used alone or in combination with other active ingredients, either simultaneously, separately or sequentially.

The compounds or compositions according to the invention may be administered in various ways or routes. The compounds or compositions of the invention may be administered by intramuscular, intravenous, intraperitoneal, cutaneous, subcutaneous, dermal, transdermal, intrathecal, ocular (for example corneal) or rectal ways, or by a topical administration on an inflammation site, and preferably by intramuscular or intravenous injection.

A typical regimen comprises a single or repeated administration of an effective amount of a TAFA4 compound over a period of one or several days, up to one year, and including between one week and about six months, or it may be chronic. It is understood that the dosage of a pharmaceutical compound or composition of the invention administered in vivo will be dependent upon the age, health, sex, and weight of the recipient (subject), kind of concurrent treatment, if any, frequency of treatment, and the nature of the pharmaceutical effect desired. The ranges of effectives doses provided herein are not intended to be limiting and represent preferred dose ranges. However, the most preferred dosage will be tailored to the individual subject, as is understood and determinable by one skilled in the relevant arts (see, e.g., Berkowet et al., eds., The Merck Manual, $16^{th}$ edition, Merck and Co., Rahway, N.J., 1992; Goodmanetna., eds., Goodman and Cilman's The pharmacological Basis of Therapeutics, $10^{th}$ edition, Pergamon Press, Inc., Elmsford, N.Y., (2001)).

The total dose required for each treatment can be administered by multiple doses or in a single dose, preferably as soon as the early symptoms of pain appear, or preventively, for example before or during surgery when needed. The pharmaceutical compound can be administered alone or in conjunction with at least one other pharmaceutical directed to the pathology, or directed to other symptoms of the pathology. Effective amounts of a compound or composition according to the invention are from about 1 µg to 100 mg/kg body weight, preferably administered at intervals of 4-24 hours for a period of several days, weeks, months, or up to 1 year, and/or any range or value therein, such as 0.001-0.01, 0.01-0.1, 0.05-100, 0.05-10, 0.05-5, 0.05-1, 0.1-100, 0.1-1.0, 0.1-5, 1.0-10, 5-10, 10-20, 20-50, and 50-100 mg/kg, for example between 0.05 and 100 mg/kg, preferably between 0.05 and 5 mg/kg, for example 0.05, 0.1, 0.2, 0.3, 0.4, 0.5, 1, 2, 3, 4 or 5 mg/kg, at intervals of 1-4, 4-10, 10-16, or 16-24 hours, for a period of 1-14, 14-28, or 30-44 days, or 1-24 weeks, or any range or value therein. A typical administration schedule comprises from 1 µg to 100 mg/kg/day.

The recipients of administration of compounds and/or compositions of the invention can be any subjects as herein defined, preferably humans.

Formulations/Concentrations

The compounds or compositions according to the invention may be administered in various forms. Thus, they may be formulated in the form of ointments, gels, pastes, liquid solutions, suspensions, tablets, gelatin capsules, capsules, suppositories (in particular for pain associated with a gastrointestinal syndrome), powders, nasal drops, or aerosols, preferably in the form of an ointment. The compounds of the invention are typically administered in the form of ointments, gels, oils, tablets, suppositories, powders, gelatin capsules, capsules, etc., optionally by means of dosage forms or devices that ensure prolonged and/or delayed release. For this type of formulation, an agent such as cellulose, carbonate or starch is advantageously used. For injections, the compounds are generally packaged in the form of liquid suspensions, which may be injected via syringes or perfusions, for example. In this respect, the compounds are generally dissolved in saline, physiological, isotonic or buffered solutions, etc., compatible with pharmaceutical use and known to the person skilled in the art. Thus, the compositions may contain one or more agents or excipients selected from dispersants, solubilizers, stabilizers, preservatives, etc. Agents or excipients that can be used in liquid and/or injectable formulations are notably methylcellulose, hydroxymethylcellulose, carboxymethylcellulose, polysorbate 80, mannitol, gelatin, lactose, vegetable oils, acacia, etc. It is understood that the flow rate and/or dose administered may be adjusted by the person skilled in the art according to the patient, the pain observed, the area to be treated, the active compound(s) concerned, the mode of administration, etc.

For topical applications, it is preferred to expose the subject to be treated to an effective amount of a pharmaceutical compound or composition according to the invention to target areas, e.g., skin surfaces, mucous membranes, and the like, which are adjacent to the peripheral neurons to be treated.

Typically, the compounds are administered at doses that may vary between about 50 µg to about 5 mg/kg of body weight of a compound of the invention, depending upon the previously mentioned criteria, whether the use is prophylactic or therapeutic and the nature of the topical vehicle employed. A preferred administration is an intramuscular, intravenous or intraperitoneal injection. Furthermore, administration by injection may comprise several (2, 3 or 4) administrations per day, if need be. In addition, for chronic treatments, delayed or prolonged systems may be advantageous, ensuring the subject effective and long-lasting pain treatment.

The invention also relates to a kit comprising (i) a TAFA4 compound or composition, as previously described, (ii) at least one additional distinct active compound efficient against pain, and optionally (iii) written instructions for using the kit.

According to a specific embodiment, the invention also relates to a kit that is suitable for treatment by the methods herein described. These kits comprise (i) a TAFA4 compound or composition, as previously described, typically in the dosages herein indicated, and (ii) a second composition containing an analgesic compound, preferably an opiate compound, in dosages generally lowered when compared to those classically prescribed, for simultaneous, separate or sequential administration, in effective amounts according to the invention.

The figures and examples illustrate the invention without limiting its scope.

EXAMPLES

I. Experimental Procedures

All animals (mice) were maintained in standard housing conditions (22° C., 40% humidity, 12 h light cycles, and free access to food and water). Special effort was made to minimize the number as well as the stress and suffering of mice used in the below experiments. All protocols are in agreement with European Union recommendations for animal experimentation.

I.1. Generation of Tafa4-GFP KI Mice with Targeted Inactivated TAFA4 Gene

To generate tafa4-GFP KI mice we used the Bacterial Artificial Chromosome (BAC)-based homologous recombination in embryonic stem cells. The final targeting vector was constructed on the basis of a 209 kb genomic clone of the mouse tafa4 locus in pBAC (RP23-427L8), obtained from a 129SVJ "BACPAC" Resources Center (BPRC) library (FIG. 2A). The bacterial recombination in the RP23-427L8 BAC vector was engineered thanks to an intermediate targeting construct that has been assembled using the plasmid vectors pL452 and pCS2/venus sv40. 109 bp of the tafa4 gene exon1 was replaced by the "YFP (Venus, hereafter GFP)-polyA loxP-EM7-PGK-Neo-loxP" cassette. The arms of homology were isolated as 271 pb and 265 pb PCR products using Taq phusion polymerase (Finnzymes). After homologous recombination of the BAC in bacteria, the final targeting construct was linearized using the AscI site and transfected into 129/SV-derived embryonic stem cells CK35. Homologous recombinant clones were identified by Southern blot using probes located at the 3' end of the construct, and by a neomycin probe. Two targeted clones were injected into C57B16/J derived blastocysts at the Immunology Center transgenic facility. Resulting chimeras were mated to C57B16/J females to produce germ line transmission of the recombinant allele.

The following oligonucleotides were used for genotyping PCRs:
GFP 436: GAAGAAGTCGTGCTGCTTCATGTG (SEQ ID NO: 28),
1585: CTGTGGAGGAAATGGTTTCAACT (SEQ ID NO: 29), and
1587: CTGCAAAGAGAAGCCAAAGCTAC (SEQ ID NO: 30).

Heterozygous males and females were mated to generate the population described in behavioral tests of the manuscript. In order to increase the visualization of GFP for cellular and molecular experiments, we also generated a TAFA4 GFP-NEO-line. The neo cassette was removed by crossing TAFA4$^{GFP/+}$ mice to a cre-deleter mouse line. The absence of neo cassette was confirmed by PCR. Except for behavioral analyses and whole-cell patch-clamp recording from spinal cord slices with attached dorsal root, Cre recombined TAFA4 GFP mice were used for all experiments.

I.2. Tissue Sections and In Situ Hybridization/Immunofluorescence

To obtain adult tissues, mice were deeply anesthetized with a mix of ketamine/xylazine and then transcardially perfused with an ice-cold solution of paraformaldehyde 4% in PBS (PAF). After dissection, they were postfixed for at least 24 h in the same fixative at 4° C. P0 were collected in ice-cold PBS 1×, gently washed, and fixed for 24 h in 4% PAF. For skin immunofluorescence, trunk skin was excised from anesthetized mice and fixed directly in 15% (v/v) acid picric-2% formaldehyde for 24 h at 4° C. Tissues were then transferred into a 30% (w/v) sucrose solution for cryoprotection before being frozen and stored at −80° C. Samples were sectioned (12 to 40 μm) using a standard cryostat (Leica). In situ hybridization and immunofluorescence were performed following standard protocols (Moqrich et al., 2004). RNA probes (Tafa4, TH, Vglut3, TrkB, MrgprD, SCG10) were synthesized using gene-specific PCR primers and cDNA templates from embryonic or adult mouse DRG. More particularly, in situ hybridization was performed using a combination of digoxigenin and/or fluorescein/biotin labeled probes. Probes were hybridized overnight at 55° C., and the slides incubated with the horseradish peroxidase anti-digoxigenin/fluorescein/biotin antibody (Roche). Final detection was achieved using a fluorescein/cy3/cy5 TSA Plus kit (PerkinElmer). For double-fluorescent in situ experiments, the first antibody was inactivated using $H_2O_2$ treatment.

The following oligonucleotides were used for the nested PCRs for probe synthesis:
tafa4-F1: TGCTCAGAAGTTCATAGCCAAA (SEQ ID NO: 5),
tafa4-R1: TAAAGGAACATTTGCAAGCTCA (SEQ ID NO: 6),
tafa4-F2: ATATGTGCAGTGTGG (SEQ ID NO: 7),
tafa4-R2+T7: TAATACGACTCACTATAGGGCAGC-CAAGTTCAAAC (SEQ ID NO: 8),
TH-F1: AAGCCAAAATCCACCACTTAGA (SEQ ID NO: 9),
TH-R1: CCGTGGAGAGTTTTTCAATTTC (SEQ ID NO: 10),
TH-R2+T7: TAATACGACTCACTATAGGGAGAGATG-CAAGTCCAATGTCCT (SEQ ID NO: 11),
Vglut3-F1: TAGCTCAGTTTCCAGGAATGGT (SEQ ID NO: 12),
Vglut3-R1: GGAGATCTAACAACATCTGATAACAC (SEQ ID NO: 13),
Vglut3-F2: CCCCCTAGAGTATCAGGAATTT (SEQ ID NO: 14),
Vglut3-R2+T7: TAATACGACTCAC-TATAGGGTGGGAAGTTTTAAAAATCTATGATTA G (SEQ ID NO: 15),
TrkB-F1: CTGAGAGGGCCAGTCACTTC (SEQ ID NO: 16),
TrkB-R1: CATGGCAGGTCAACAAGCTA (SEQ ID NO: 17),
TrkB-F2: CAGTGGGTCTCAGCACAGAA (SEQ ID NO: 18),
TrkB-R2+T7: TAATACGACTCACTATAGGGCTAGGAC-CAGGATGGCTCTG (SEQ ID NO: 19),
MrgprD-F1: GGGCATCAACTGGTTCTTACTC (SEQ ID NO: 20),
MrgprD-R1: AGGGATTGTCTTGACTGTCG (SEQ ID NO: 21),
MrgprD-F2: AACGGGATGTGAGGCTACTTTA (SEQ ID NO: 22),
MrgprD-R2+T7: TAATACGACTCACTATAGGGATTTAT-GCCTTGACTTCCCTGA (SEQ ID NO: 23),
SCG10-F1: GCAATGGCCTACAAGGAAAA (SEQ ID NO: 24),
SCG10-R1: GGCAGGAAGCAGATTACGAG (SEQ ID NO: 25),
SCG10-F2: AGCAGTTGGCAGAGAAGAGG (SEQ ID NO: 26), and
SCG10R2+T7: TAATACGACTCACTATAGGGGGCAG-GAAGCAGATTACGAG (SEQ ID NO: 27).

For immunofluorescence, primary antibodies were diluted in PBS-10% donkey or goat serum (Sigma)-3% bovine albumin (Sigma)-0.4% Triton X-100 and incubated overnight at 4° C. Primary antibody concentrations and references are: rabbit anti-TrkA 1:1000 (Interchim), goat anti-TrkC 1:1000 (R&D Systems), goat anti-Ret 1:500 (R&D Systems), rabbit anti-CGRP 1:2000 (Chemicon), chicken anti-green fluorescent protein (GFP) 1:1000 (Ayes Labs), rabbit anti-PKCγ 1:1000 (Santa Cruz Biotechnology), anti-S100 1:400 (Dako), and goat anti-parvalbumin 1:1000 (Swant). Corresponding donkey or goat anti-rabbit, anti-chick, and anti-goat Alexa 488, 555, or 647 (Invitrogen or Molecular Probes antibodies) were used for secondary detection. Isolectin D34 conjugates to Alexa FluorR 568 dye were used at 1:100 (Invitrogen).

I.3. Cell Counts and Statistical Analysis.

12 μm serial sections of thoracic (T12) and lumbar (L4) DRG were distributed on six and eight slides respectively and subjected to different markers including the pan-neuronal marker SCG10. This approach, in addition to providing the total number of neurons, allowed us to represent all counts as a percentage of SCG10$^+$ neurons. For each genotype, two to four DRG were counted in at least three independent mice. Statistical significance was set to $p<0.05$ and assessed using one-way ANOVA followed by unpaired t-test.

I.4. Electrophysiological Recording and Calcium Imaging

Whole-cell patch-clamp recording of cultures of DRG neurons and from spinal cord slices with attached dorsal root as well as calcium imaging protocols are described below.

Cultures of DRG Neurons for Patch Clamp Recording 7 to 14 week old heterozygous or TAFA4-null male mice were anesthetized with halothane and sacrificed by severing of the carotid arteries in accordance with the Guide for the Care and Use of Laboratory Animals. Dissociation and cultures of DRG neurons were realized from lumbar DRGs excised and freed from their connective tissue sheaths as previously described (Hao and Delmas, 2010, 2011). They were incubated in enzyme solution containing 2 mg/ml of collagenase IA for 45 min at 37° C. and triturated in Hanks' medium (GIBCO BRL). The resulting suspension was plated in Nunclon dishes coated with 10 ng/ml laminin (Sigma). Culture medium was Dulbecco's modified Eagle's medium (DMEM) supplemented with 10% heat-inactivated FCS, 100 U/ml penicillin-streptomycin, 2 mM l-glutamine, 25 ng/ml nerve growth factor (NGF7S, Sigma-Aldrich, France), and 2 ng/ml glial-derived neurotrophic factor (GDNF, Invitrogen, France) (all from GIBCO BRL). Neurons were maintained in a humidified atmosphere (5% $CO_2$, 37° C.) for 12 h before recording.

Whole-Cell Patch-Clamp Recording

Patch clamp recordings were performed using borosilicate electrodes having resistances ranging from 2 to 3 MΩ. Recording of Nav1.8 and ICaT used a CsCl-based pipette solution consisting of (mM): 125 CsCl, 10 HEPES, 5 NaCl, 0.4 NaGTP, 4 MgATP, 1 $MgCl_2$, 4.8 $CaCl_2$ and 10 EGTA (adjusted to pH 7.3 with CsOH). IKA, h-current and MA currents were recorded using a KCl-based pipette solution containing (mM): 134 KCl, 10 HEPES, 4 MgATP, 0.4 NaGTP, 1 $MgCl_2$, 4.8 $CaCL_2$ and 10 EGTA (pH 7.3). The same KCl-based pipette solution was used for current-clamp recording. The standard external solution consisted of (mM): 132 NaCl, 1 KCl, 1 $MgCl_2$, 2.5 $CaCl_2$, 10 HEPES, 10 D-glucose and TTX (500 nM, Ascent Scientific) (adjusted to pH 7.3 with NaOH, 300 mOsm/l). Neurons were perfused with bath solution at a flow rate of 2-3 ml/min.

Mechanical Stimulation

Mechanical stimulation using piezoelectrically driven mechanical probes has been detailed elsewhere (Hao and Delmas, 2010). Briefly, a fire-polished glass micropipette cemented to a piezo-electric actuator (Step Driver PZ-100; Burleigh) was used as a mechanical probe and positioned at an angle of 45° from horizontal. Downward movement of the probe toward the cell was driven by pClamp program (Molecular Devices). The probe had a velocity of 800 μm/s (unless otherwise noted) during the ramp segment of the command for forward motion, and the stimulus was applied for durations ranging from 200 ms to several seconds. Unless otherwise noted, voltage-clamped MA currents were recorded at a holding potential of −100 mV.

The time constants of MS current decay were fitted to exponentials using the Chebyshev nonlinear least square fitting procedure (Hao and Delmas, 2010). Current traces were fitted with either monoexponential or bi-exponential functions. Bi-exponential functions were as follows: $I(t)=A1 \cdot exp(-t/\tau 1)+A2 \cdot exp(-t/\tau 2)+Ao$, where $\tau 1$ and $\tau 2$ represent the rapid and slow exponential components, A1 and A2 represent the amplitude of each respective component, and Ao represents the baseline current. Fits with greater than two exponential components did not significantly enhance description of the current decay, as judged by residual analysis. Cells were classified as expressing a particular MS cation current if the main component (≥80%) of the current evoked at −100 mV declined monoexponentially. MS currents not meeting this requirement were classified as mixed. Based on current decay time constants, three types of MS currents could be distinguished: rapidly adapting currents (IR, 3-6 ms), slowly adapting currents (IS, 200-300 ms) and ultra-slowly adapting currents (IuS, 1000 ms).

Data Acquisition and Analysis

Voltage and current recordings were made using an Axopatch 200B amplifier (Molecular Devices), filtered at 1 kHz, and sampled at 40-100 μs. Voltage errors were minimized using 75-85% series resistance compensation. Cell capacitance was estimated from the time constant of the decay phase of a current transient elicited by a 10 mV hyperpolarizing step. All experiments were done at room temperature. PRISM 4.0 (GraphPad) software was used to perform data analysis. Results are presented as mean±SEM and n represents the number of neurons examined. Statistical analysis used Student's t-test and P<0.01 was considered statistically significant.

Whole-Cell Patch-Clamp Recording from Spinal Cord Slices with Attached Dorsal Root Transverse spinal cord slices with attached dorsal roots from juvenile (P21 to P34) TAFA4-null and WT mice were prepared for whole-cell recording following the protocol described in Mourot et al. (2012). Mice were deeply anesthetized with isoflurane before being quickly beheaded. A piece of tissue containing the spinal column and surrounding muscles was quickly removed and immersed in ice-cold oxygenated low-calcium artificial cerebrospinal fluid (ACSF) (in mM: NaCl 101; KCl 3.8; $MgCl_2$ 18.7; $MgSO_4$ 1.3; $KH_2PO_4$ 1.2; HEPES 10; $CaCl_2$ 1; glucose 1). After laminectomy, the spinal cord was gently removed and its lumbar part was placed into a small 3% agarose block. Spinal slices (300 μm thick) were cut using a Leica VTS1000 vibratome, and transferred into warm (31° C.) ACSF (in mM: NaCl 130.5; KCl 2.4; $CaCl_2$ 2.4; $NaHCO_3$ 19.5; $MgSO_4$ 1.3; $KH_2PO_4$ 1.2; HEPES 1.25; glucose 10; pH 7.4) equilibrated with 95% $O_2$-5% $CO_2$ for at least one hour before starting patch clamp recordings. Spinal slices were placed in a recording chamber bathed with warmed (31° C.) ACSF. Electrophysiological measurements were performed under the control of an Olympus BX51 microscope using a 2B multiclamp (Molecular Devices). Patch pipettes (7-11 S2) were filled with appropriate pipette solution (in mM: K-gluconate 120; KCl 20; $CaCl_2$ 0.1; $MgCl_2$ 1.3; EGTA 1; HEPES 10; GTP 0.1; cAMP 0.2; Leupeptin 0.1; Na2ATP 3; D-Manitol 77; pH 7.3). For the measurement of T-type calcium currents, the patch pipette had the following concentrations (in mM: Cs methanesulfonate 120; CsCl 20; $CaCl_2$ 0.1; $MgCl_2$ 1.3; EGTA 1; HEPES 10; GTP 0.1; cAMP 0.2; leupeptin 0.1; Na2ATP 3; D-mannitol 77; pH 7.3), and TTX (0.5 μM), CNQX (5 μM), DL-APV (10 μM), strychnine (10 μM), bicuculline (5 μM) and TEA (2.5 mM) were added to the ACSF in order to block sodium voltage activated and synaptic currents. A glass suction electrode connected to a Master 8 (A.M.P. Instruments Ltd.) stimulator was used to stimulate dorsal roots. Typically, high duration (500 μs), high intensity (350 μA) stimulations were used to recruit most primary afferent fibers in the recorded slice. Liquid junction potentials (calculated value −16.5 mV) are not corrected for.

Molecular Identification of Spinal Lamina IIi Recorded Interneurons

To determine the neurotransmitter phenotype of recorded lamina II neurons, biocytin was added 0.5% to the pipette recording solution. At the end of the recordings, the patch pipette was carefully removed to preserve as much as possible the integrity of the recorded neurons. Spinal slices were then fixed overnight at 4° C. in 4% PFA and kept at −4° C. in 0.5% PFA for later revelation of biocytin and GAD. The slices were rinsed 3 times in PBST and incubated in primary antibody (anti-GAD6567, Sigma G5163, 1/2000 in PBST 0.5% BSA) for 48 hours at 4° C. The slices were rinsed 3 times in PBST and incubated overnight in a mix of secondary antibody (goat anti-rabbit Alexa 568, Molecular Probes A-11011, 1/500) and streptavidin Alexa 488 (Invitrogen S-11266, 1/500). The slices were rinsed 3 times in PBST and mounted in Dako fluorescent mounting medium. Acquisitions were performed on a Leica SPE confocal microscope using ×63 oil immersion objectives.

Ca2+ Imaging

Lumbar DRG neurons from heterozygote or knockout 7 to 14 week old TAFA4 mice were seeded on laminin coated glass-bottom chambers (FluoroDish, WPI) and cultivated for 16-22 hours at 37° C. in B27 supplemented Neurobasal A medium (Invitrogen, France) with 100 ng/ml NGF 7S (Sigma-Aldrich, France), 2 ng/ml GDNF (Invitrogen, France), and 10 ng/ml NT4 (PeproTech, France). Calcium imaging was performed 12-17 hours after seeding. Prior to recording, neurons were incubated with 5 µM fura-2AM in Tyrode's solution for 1 hour at 37° C. Fluorescence measurements were made with an inverted microscope (Olympus IX70) equipped with a CoolSNAP HQ camera (Roper Scientific, France). Fura-2 was excited at 340 nm and 380 nm and ratios of emitted fluorescence at 510 nm were acquired simultaneously with bath temperature using MetaFluor software (Universal Imaging). Temperature was controlled with a gravity driven perfusion (1-2 ml/min) cooled with a Peltier device mounted in series with a resistive heater (CellMicroControls). Perfusion was first cooled at 12° C. than heated at 37° C. before application onto the chamber. Temperature was monitored with a thermistor probe located near the perfusion outlet always at the same place. Rapid cooling from 37° C. to less than 15° C., achieved by switching off the heating, took typically less than 40 sec. Pharmacological agonists of several transient receptor ion channels (100 µM menthol, 100 µM allyl isothiocyanate (AITC), 0.5 µM capsaicin, 10 µM pregnenolone sulfate) were prepared into the Tyrode's solution and applied sequentially to the neurons for a few seconds at 37° C. For iso- and hypotonic stimulations, the extracellular solutions were prepared keeping constant the concentration of NaCl and varying the level of mannitol to control the osmolarity. The isotonic solution (300 mOsm) contained (in mM): 87 NaCl, 100 mannitol, 3 KCl, 1 $MgCL_2$, 2.5 $CaCl_2$, 10 HEPES, and 10 glucose, and the hypotonic solution (200 mOsm) contained (in mM): 87 NaCl, 51 mannitol, 3 KCl, 1 $MgCl_2$, 2.5 $CaCl_2$, 10 HEPES, and 10 glucose. Data were analysed offline using MetaFluor, Excel, and GraphPad Prism.

II. Behavioral Assays

All behaviour analyses (Open field, Rotarod, Hot plate, Cold plate, Thermal gradient, Two-temperature choice, Thermal nociceptive threshold (Hargreaves' test), Itch test, Von Frey, Dynamic Von Frey and Formalin test) were conducted on littermate males 8-12 weeks old. Detailed description of all these tests is provided below. Complete Freund's adjuvant (CFA) and carrageenan hindpaw injection, intrathecal injection of recombinant TAFA4 and chronic constriction of the sciatic nerve (CCI) are also described below. Student's t-test was used for all statistical calculations.

More particularly, all behavioral assays were conducted on littermates 8-12 weeks of age of mixed C57BL6/129SV genetic background. Animals were acclimated for 20 minutes to their testing environment prior to all experiments, which were done at room temperature (−22° C.). Experimenters were blind to the genotype of the mice during testing. Student's t-test was used for all statistical calculations. All error bars represent standard error of the mean (SEM). General behavioral (locomotor and learning activity) was measured using a rotarod apparatus (LSI Letica Scientific Instruments). Gradient, thermal plates, open field, Hargreaves' and Von Frey apparatus were from Bioseb.

II.1. General Behavioral Assays

II.1.A. Open Field Test

The open field test is commonly used to assess locomotor, exploratory and anxiety-like behavior. It consists of an empty and bright square arena (40×40×35 cm), surrounded by walls to prevent the animal from escaping. The animals were individually placed in the center of the arena and their behavior recorded with a video camera over a 5-minute period. Anxiety-related behavior is measured by the degree to which the rodent avoids the center area (20×20 cm), analysed by Bioseb tracking software.

II.1.B. Rotarod Test

A rotarod apparatus (LSI, Letica Scientific Instruments) was used to explore coordinated locomotor, balance and learning function in mice. Mice were placed on a rod that slowly accelerated from 4 rpm to 44 rpm constant speeds of rotation over 5 min, and the latency to fall off during this period was recorded. The test was done 4 consecutive days. Each day, the animals were tested three times separated by at least a 5 min resting period. Response to temperature choice test and response to temperature gradient assay were performed as described in Moqrich et al. (2005) but using a Bioseb apparatus.

II.2. Thermal Sensitivity Tests

II.2.A. Hot Plate

To assess heat sensitivity, mice were confined individually to a metal surface maintained at 48°, 50° or 52° C. by a Plexiglass cylinder 20 cm high, and the latency to nociceptive responses (licking, shaking or jumping of hind paws) measured. To prevent tissue damage, mice were removed from the plate immediately after a nociceptive response or after a maximum of 90 s, 60 s and 45 s respectively. Each mouse was tested two times with a latency of 5 min between each test; the withdrawal time corresponds to the mean of the two measures. A latency of at least 1 h between each tested temperature was respected.

II.2.B. Cold Plate

To test cold sensitivity, mice were placed individually into a Plexiglass chamber maintained at 22°, 10° or 4° C. The rearing time of the mice during the first minute is measured. Each mouse is exposed three times to each temperature with a minimum five-minute resting period between trials and one hour separating periods between temperatures.

II.2.C. Thermal Gradient Test

This test has been described previously (Moqrich et al., 2005). Briefly, mice were individually tracked for 90 min in four separate arenas of the thermal gradient apparatus (Bioseb). A controlled and stable temperature gradient of 14° C. to 53.5° C. was maintained using two Peltier heating/cooling devices positioned at each end of the aluminum floor. Each arena was virtually divided into 15 zones of equal size (8 cm) with a distinct and stable temperature. The tracking was performed using a video camera controlled by the software provided by the manufacturer.

II.2.D. Two-Temperature Choice Tests

Two mice were placed simultaneously in each lane of the two-temperature choice apparatus (Bioseb). Mice were tracked for 10 min using the Bioseb software. During the first day, both plates were kept at 20° C. for 10 min. Days after this acclimatizing period, 2 plates were individually warmed or cooled to different temperature (42° C. to 16° C.) and kept at the appropriate temperature for the 10 min test. A 1 h time lapse was respected between 2 different tests.

II.2.E. Thermal Nociceptive Threshold (Hargreaves' Test)

To assess hind paw heat sensitivity, Hargreaves' test was conducted using a plantar test device (Bioseb). Mice were placed individually into Plexiglass chambers on an elevated glass platform and allowed to acclimatize for at least 30 minutes before testing. A mobile radiant heat source of constant intensity was then applied to the glabrous surface of the paw through the glass plate and the latency to paw withdrawal measured. Paw withdrawal latency is reported as the mean of three measurements for both hind paws with at least a 5 min pause between measurements. IR source was adjusted to 20% and a cut-off of 20 s was applied to avoid tissue damage.

II.3. Mechanical Sensitivity Testing

II.3.A. Dynamic Von Frey

To assess hind paw mechanical sensitivity, the dynamic Von Frey test was conducted using a Bioseb apparatus. Von Frey filament is applied with an increasing strength up to 7 g for 20 s.

Injected and non-injected hind paws are pinched three times with at least 5 min of latency between and the average of withdrawal (g or second) is calculated.

II.3.B. Von Frey Filament Test

For the chronic constriction model, we used the Von Frey hair filaments of three different bending forces (0.07, 0.6 and 1.4 g). For the carrageenan model, mechanical allodynia and hyperalgesia were assessed using the Von Frey hair filaments of four different bending forces (0.07, 0.4, 0.6 and 1.4 g). For details, see the "Unilateral peripheral mononeuropathy" and "Carrageenan injection" paragraphs.

II.4. Chemical Sensitivity Testing

II.4.A. Formalin Test

Formalin solution was prepared at 2% in PBS 1× from a formalin stock (Fisher Scientific) (note that formalin stock corresponds to a 37% formaldehyde solution). Mice were housed individually in Plexiglass chambers and allowed to habituate to the testing environment for 30 minutes. Following subcutaneous injection of 10 µl of formalin in the left hind paw, the animals were immediately placed individually in observation chambers and then monitored for pain behavior (shaking, licking and biting of the injected paw) for 60 min. The pain behavior cumulative time of the injected paw was counted at 5-minute intervals. Time spent exhibiting these pain behaviors was recorded for the first phase (0-10 min) and the second phase (10-60 min).

II.4.B. Itch Test Using Pruritogenic Agent 48/80

Pruritogenic agent 48/80 (Sigma-Aldrich, C2313) was prepared at 2 µg/µl in PBS 1×. 100 µg (50 µl) were injected into the mouse's neck. The itching cumulative time was counted for 40 minutes.

II.4.C. CFA Injection

10 µl of complete Freund's adjuvant (CFA) was injected into the left hind paw of anesthetized mice using a Hamilton syringe, in order to produce inflammation and alterations in nociceptive sensitivity. Injected paws were assessed for signs of acute inflammation, such as edema and redness, 24 hours after injection. The responses to thermal and mechanical stimuli were measured before injection (Day0), as well as one, three and seven (only for mechanical) days after CFA injection. The uninjected right hind paws served as a control.

II.4.D. Carrageenan Injection

20 µl of 1% λ-Carrageenan (Sigma-Aldrich, 22049-5G-F) in PBS1× was injected into the mouse's left hind paw using a Hamilton syringe.

For the carrageenan model, mechanical allodynia and hyperalgesia were assessed before and after injection using the Von Frey hair filaments of four different bending forces (0.07, 0.4, 0.6 and 1.4 g). For each filament, two times five stimuli were applied with an interval of 3 to 5 seconds. The uninjected right hind paws served as a control.

II.4.E. Unilateral Peripheral Mononeuropathy

For the chronic constriction of the sciatic nerve (CCI) model, unilateral peripheral mononeuropathy was induced in mice anaesthetized with Ketamine (40 mg/kg ip) and Xylasine (5 mg/kg ip) with three chromic gut (4_0) ligatures tied loosely (with about 1 mm spacing) around the common sciatic nerve (Bennett and Xie, 1988).

The nerve was constricted to a barely discernable degree, so that circulation through the epineurial vasculature was not interrupted (Descoeur et al., 2011). For the chronic constriction model, mechanical allodynia and hyperalgesia were assessed before the surgery and every other 5 days post-surgery using the Von Frey hair filaments of three different bending forces (0.07, 0.6 and 1.4 g). For each filament, two times five stimuli were applied with an interval of 3 to 5 seconds.

II.4.F. Intrathecal Injection of Recombinant TAFA4

Intrathecal (i.t.) injections of TAFA4 (200 µg/ml, human recombinant TAFA4, R&D Systems) or vehicle (PBS) in a volume of 10 µl were done 15 min before the formalin test. Mice were held in one hand by the pelvic girdle and a 25-gauge needle connected to a 20 µl Hamilton syringe was inserted into the subarachnoidal space between lumbar vertebrae L5 and L6, until a tail-flick was elicited.

III. Results

III.1. TAFA4 is a Specific Marker of C-LTMRs

Interestingly, the inventors have found that Tafa4 transcripts were highly enriched in adult DRG and trigeminal neurons. Using in situ hybridization, the inventors have demonstrated that Tafa4 transcripts are expressed in approximately 8% and 19% of total lumbar (L4) and thoracic (T12) adult DRG neurons, respectively (FIG. 1A). Double fluorescent labeling experiments showed that Tafa4 is completely excluded from TrkA$^+$ neurons and identifies a subset of Ret$^+$ neurons (FIGS. 1C and 1D). TAFA4$^+$ neurons do not bind IB4 and are completely distinct from mrgprd$^+$ neurons (FIGS. 1E and 1F). In contrast, TAFA4 is predominantly co-expressed with TH and VGLUT3 (FIG. 1G). Using VLUT3-EGFP DRG sections (Seal et al., 2009), the inventors have found that 92+/−4% of TAFA4$^+$ neurons co-express EGFP and 94+/−6% of EGFP$^+$ neurons co-express TAFA4 (FIG. 1H), identifying TAFA4 as a specific marker of C-LTMRs. In contrast to TH and VGLUT3, TAFA4 is almost restricted to DRG and trigeminal neurons with a low expression in central nervous system neurons, namely in the habenula and in scattered populations of neurons in the nuclei of the brain stem and hypothalamus.

III.2. TAFA4-Expressing Neurons Display Properties of Mechano-Nociceptors

To investigate the role of TAFA4 in C-LTMRs, the inventors have generated a knock-in mouse model that allows the genetic labeling of TAFA4-expressing neurons while eliminating TAFA4 protein in a targeted manner (i.e., without affecting unknown genes) (FIG. 5A). The inventors first confirmed that TAFA4 transcripts were completely abolished in TAFA4$^{GFP/GFP}$ homozygous mice (herein TAFA4-null mice) (FIGS. 5B and 5C). GFP$^+$ neurons projected to the innermost layer of lamina II centrally and exclusively innervated the hairy part of the skin peripherally (FIGS. 5G-5J).

Using patch-clamp recordings and calcium imaging, the inventors have found that GFP$^+$ neurons displayed many properties of C-unmyelinated nociceptors, including small cell capacitance, high input resistance, short duration action potential devoid of a prominent hump in the repolarizing phase, and a remarkable concomitant expression of TTX-resistant Nav1.8, low-threshold T-type Ca$^{2+}$ (ICa$_T$), A-type K$^+$ current (IK$_A$) and hyperpolarization-activated h (I$_h$) currents (FIGS. 2A-2C). ICa$_T$-mediated rebound potentials were also typically observed at repolarization (FIG. 2D). The activation of IK$_A$ resulted in a delay in the occurrence of action potentials (APs) or rebound potentials in response to positive or negative current steps, respectively (FIGS. 2D and 6). The homogeneous presence of these different currents shapes the cell firing in a unique way, with a depolarizing "sag" response to negative current steps due to I$_h$ and a "gap" in AP firing in response to depolarizing current steps. These firing properties can be used as specific criteria to classify TAFA4-expressing neurons.

GFP$^+$ neurons did not respond to many putative nociceptive agents, including capsaicin, menthol, pregnenolone sulfate and 5HT or to rapid cooling (FIG. 2E). In contrast, GFP$^+$ neurons displayed differential responses to the TRPA1 agonist allyl isthiocyanate (AITC) and to hypo-osmotic solution (FIG. 2E), suggesting some functional heterogeneity within C-LTMRs.

Classical features of C-LTMRs, including slow conduction velocities, trains of spikes in response to a light mechanical force and slow adaptation to a sustained mechanical stimulus, have been determined using ex-vivo skin nerve preparations (Bessou et al., 1971; Li et al., 2011; Seal et al., 2009; Woodbury et al., 2001). Application of mechanical forces to the cell body of GFP$^+$ neurons revealed the presence of mechanically-activated (MA) cation currents in 95% of neurons tested (FIGS. 2F and 2G). Although rapidly adapting MA currents could be occasionally encountered (15%), slowly and ultra-slowly adapting MA currents were predominant (21.3 and 57.9%, respectively) in GFP$^+$ neurons (FIG. 2F). All these currents were cationic and non-selective, with reversal potential ranging from −2 to +4 mV. Consistent with the slow adaptation properties of MA currents, slow velocity ramp stimulus was able to trigger APs (FIG. 2G), indicating that mechanosensory GFP$^+$ neurons respond to slow motion stimuli.

In conclusion, all the above expression data, combined with calcium imaging and electrophysiological recordings, demonstrate that TAFA4$^+$ neurons display physiological properties of C-unmyelinated mechano-nociceptors.

III.3. TAFA4-Null Mice Develop Severe Injury-Induced Mechanical and Chemical Hypersensitivity To gain insight into the functional role of TAFA4 in C-LTMRs, the inventors have subjected TAFA4-null mice to a large battery of somatosensory tests under acute, inflammatory and neuropathic pain conditions. TAFA4-null mice appeared normal in terms of body weight, open-field (FIG. 6A) and rotarod (FIG. 6B) profiles, demonstrating that TAFA4-null mice do not have abnormalities in motor activity or anxiety. The inventors found no difference between WT and TAFA4-null mice in the hot plate (FIG. 6C), thermotaxis gradient assay (FIG. 6D) or Hargreaves' test (FIG. 6E) as well as in the cold plate, the two-temperature choice and the dynamic cold and hot plate tests. Then the inventors tested TAFA4-null mice for ability to sense mechanical stimuli under acute, inflammatory and neuropathic pain conditions.

In the complete Freund's adjuvant (CFA) model, mechanical sensitivity was measured using the automated Von Frey apparatus (FIG. 3A). Both genotypes exhibited a significant decrease of withdrawal threshold for the treated paw 24 hours after CFA injection. When tested 3 days post-CFA, TAFA4-null mice exhibited a significantly lower withdrawal threshold compared to WT mice.

Complete recovery for both genotypes was achieved 7 days post-inflammation. To further explore the role of TAFA4 in mechanical sensitivity, the inventors used Von Frey filaments in response to carrageenan (FIGS. 3B-3E). Consistent with the CFA model, TAFA4-null mice exhibited prolonged pain hypersensitivity in response to all tested filaments at 3 and 7 days post treatment. Very interestingly, TAFA4-null mice displayed enhanced mechanical hypersensitivity as early as 1 and 3 hours post-carrageenan treatment with all filaments including the finest calibers (0.07 and 0.4 g), suggesting an important role of TAFA4 in tactile allodynia (FIGS. 3B-3E).

Finally, to assess the role of TAFA4 in neuropathic pain, the inventors used the chronic constriction of the sciatic nerve (CCI) model (FIGS. 3F-3H). TAFA4-null mice exhibited a prolonged mechanical hypersensitivity phenotype for all tested filaments, demonstrating a role for TAFA4 in neuropathic pain.

III.4. Human Recombinant TAFA4 Completely Reversed Mechanical and Formalin-Induced Pain Hypersensitivity in TAFA4 Null-Mice Intrathecal administration of 2 μg of human recombinant TAFA4 seven days post-carrageenan or 30 days post-CCI reversed both hypersensitivity phenotypes observed in TAFA4-null mice to WT levels (FIGS. 3B-3H, day7+TAFA4 and day30+TAFA4).

To test whether the enhanced mechanical hypersensitivity in TAFA4-null mice was modality specific, the inventors carried out the formalin test (FIGS. 3I and 3J). Intraplantar injection of 10 μl of 2% formalin triggered a robust first pain response in both genotypes. TAFA4-null mice exhibited a dramatically elevated response in the second phase, suggestive of an enhanced central sensitization in these mice. Importantly, formalin-induced hypersensitivity in TAFA4-null mice was reversed to WT levels after intrathecal administration of TAFA4 fifteen minutes before formalin injection (FIG. 3K).

Taken together, the above results demonstrate that TAFA4 is required to maintain the normal threshold of injury-induced mechanical and chemical pain hypersensitivity.

III.5. Lamina IIi Neurons Exhibit Increased Excitability in TAFA4 Null-Mice

To further explore the central sensitization phenotype induced by loss of TAFA4, the inventors performed whole-cell recordings of lamina IIi neurons in dorsal root-attached spinal cord slices from WT (n=19) and TAFA4-null mice (n=25). However, injection of depolarizing current pulses of increasing amplitudes (0-50 pA) elicited more action potentials in TAFA4-null neurons than in WT (FIGS. 4A1 and 4A2, ANCOVA, p<0.001). This effect was even more pronounced at the onset of the depolarizing current pulse, as TAFA4-null neurons showed increased discharge frequency at the beginning of the current pulse, before adapting to discharge rates comparable to those of WT neurons (FIG. 4A3). Furthermore, injection of hyperpolarizing current pulses (−50 or −25 pA) elicited higher rebound AP in TAFA4-null neurons compared to WT (FIGS. 4A1 and 4A4, p=0.049 and p=0.001, respectively). Together, these data demonstrate an increased excitability of lamina IIi neurons in TAFA4-null mice.

The differences observed in TAFA4-null mice show a differential regulation of slowly inactivating low threshold currents. To characterize these currents, the inventors measured the outward current elicited at −40 mV in lamina IIi neurons using a symmetrical voltage ramp protocol (−40 to −120 and back to −40 mV). Whereas in WT neurons an outward current with slow desensitization could be observed at the end of the rising voltage ramp, this current was almost absent in TAFA4-null neurons (FIGS. 4B1 and 4B2, p=0.001). As intrathecally administered recombinant TAFA4 diminishes the exaggerated pain behavior in injured TAFA4-null mice, the inventors examined the effects of adding recombinant human TAFA4 on lamina Iii neurons from TAFA4-null mice. The inventors found that exogenous application of TAFA4 (20-30 mn, 20 nM) induced the expression of an outward current, similar to that observed in neurons from WT animals in control conditions (i.e., without TAFA4) (FIGS. 4C1 and 4C2, n=19, p<0.001). This current was not affected by external TEA (2.5 mM, n=3), but was completely blocked by 4AP (1 mM), thus demonstrating that A-type current pharmacology is involved, i.e., potassium ionic channels. These effects were specific to TAFA4, as addition of recombinant TAFA5 (n=5, FIGS. 4D1 and 4D2) or TAFA2 (n=6, FIG. 4D2) could not elicit this low threshold outward current from TAFA4-null neurons.

Following TAFA4 addition, the distribution of outward current intensities among lamina IIi neurons was best fitted by a mix of two Gaussian curves, revealing the existence of two distinct populations: one-third of the neurons displayed significant outward currents while the remaining neurons were weakly or not affected by TAFA4 bath application (FIG. 4E1). Phenotypic characterization of TAFA4-responsive neurons showed that TAFA4 elicited similar outward currents both in GAD-positive and GAD-negative neurons (FIG. 4E2).

The experimental data show that TAFA4 depresses a subset of glutamergic excitatory (GAD−) and GABAergic inhibitory interneurons (GAD+), preferably by the activation of a low threshold outward currents. In particular, as excitatory transmission seems to dominate sensory processing in spinal cord substancia gelatinosa (corresponding to spinal cord lamina II), the net result of such a dual depression of GABAergiques and glutamergic neurons by TAFA4 would be dominated by a decrease in excitatory transmission, thereby reducing the amount of nociceptive information transmitted to lamina I projection neurons. Thus, TAFA4 compound according to the invention, reduces nociceptive information by decreasing excitatory transmission in spinal cord interneurons.

Among low threshold currents, Ih and T-type calcium currents may also shape the firing of lamina Iii neurons. To characterize Ih-like currents in WT and TAFA4-null mice, the inventors quantified the hyperpolarization evoked sag by measuring the difference between peak and steady-state potentials in response to a hyperpolarizing current pulse (FIG. 7B1). The inventors found that isolated T-type currents evoked by square potential pulses (see methods) were frequently weaker in WT than in TAFA4-null mice (FIG. 7C1). Statistical analysis revealed a significant increase in T-type current densities in TAFA4-null lamina IIi neurons compared to WT (FIG. 7C2; p=0.001).

Taken together, the above results indicate that TAFA4 modulates the intensity of low-threshold outward currents in lamina IIi neurons, directly or indirectly.

IV. Analgesic Effect of Intrathecal TAFA4 in Animals with Neuropathic Pain

IV.1. Neuropathic Pain Model SN1

The SNI model (Spared Nerve Injury, developed by Decosterd and Woolf, 2000; Pain, Vol. 87, p 149-158) was used. The SNI model consists of the transection of tibial branches and of the common peroneal nerve of the sciatic nerve, the sural nerve remaining intact. The latter then develops signs of neuropathic pain with substantial mechanical allodynia. The SNI model has many advantages:

Neuropathic pain is persistent. This allows the grasp of habituation phenomena upon repeated injections of TAFA4.

The generated pain is robust.

The model is very reproducible.

IV.2. Dose-Effect Study

In order to determine the optimal concentration, a first test was conducted on a "fast" inflammatory pain model (1% carrageenan).

Procedure:

18 eight-week-old male TAFA4-KO mice are used.

Recombinant human TAFA4 (#5099-TA, R&D, batch #PXC0213101) is resuspended in 0.9% NaCl at 3 different concentrations (12.5 µg/mL, 50 µg/mL and 200 µg/mL).

Von Frey filament measurement with the up/down method for determining the baseline.

Intraplantar injection of 20 µl of carrageenan (1%) in a hind paw.

Measurement of the response threshold 4 h after injection to check for the occurrence of inflammatory pain.

24 h later, a new measurement is made.

Then blind intrathecal injection of 10 µl of TAFA4 solution at 3 different concentrations (n=6 to 12.5 µg/mL; n=5 to 50 µg/mL; n=6 to 200 µg/mL) is performed.

Measurement of the response threshold is made 30 minutes after injection.

Results:

The results are shown in FIG. 8. Occurrence of mechanical allodynia is observed 4 hours after injection of carrageenan, and is maintained 24 h later. Injection of 10 µl of each of the TAFA4 solutions induced a strong increase in the threshold response to Von Frey filaments. The three tested concentrations induced a statistically significant reduction in the pain induced by carrageenan (* p<0.05).

These concentrations (12.5, 50 and 200 µg/mL) were used for subsequent testing of the analgesic effect of TAFA4 by intrathecal injection in the SNI neuropathic pain model.

IV.3. Intrathecal Injection in SNI Animals

Procedure:

The experiments are conducted on eight-week-old WT C57B16 mice. 42 mice were used. Recombinant human TAFA4 (#5099-TA, R&D, batch #PXC0213101) is resuspended in 0.9% NaCl at 3 different concentrations (12.5 µg/mL, 50 µg/mL and 200 µg/mL). A 200 µg/mL BSA solution is used as a negative control. After having measured the base threshold of the mice with Von Frey filaments by the up/down method, the SNI module is set into place. The mice are anesthetized, ligature of the tibial nerve and the fibular nerve is put into practice and these two nerves are then severed. The sural nerve left intact develops neuropathy quite rapidly. 3 days after surgery, occurrence of neuropathy is ascertained. A decrease of the response threshold to Von Frey filaments of the ipsilateral paw is thereby observed. 7 days after surgery, the response threshold is again measured. 10 µl of each of the 3 TAFA4 solutions (n=10 at 12.5 µg/mL; n=10 at 50 µg/mL; n=9 at 200 µg/mL) and of BSA solution (n=10) are then blind-injected intrathecally.

The response threshold is measured 30 minutes, 2 hours, 4 hours, 6 hours and 24 hours after injection.

Results:

The results are presented in FIG. 9. After intrathecal injection, a significant increase of the response threshold for the three TAFA4 solutions was observed as soon as 30 minutes after injection. On the other hand, injection of BSA had no effect on the response threshold of the mice. After 2 h, the analgesic effect was maintained at its maximum for the three concentrations. After 4 h, mice having received an injection of 2 µg TAFA4 still exhibited a high response threshold (**: $p<0.01$; *: $p<0.05$). We also monitored the response of contra-lateral paws following intrathecal injection of TAFA4 or BSA solutions, and no statistical difference was observed (see FIG. 10).

These results show that intrathecal injection of the three tested TAFA4 concentrations caused a substantial comparable analgesic effect on neuropathic pain. The effect of the strongest concentration (200 µg/ml, i.e., 2 µg of TAFA4) lasts longer. Furthermore, TAFA4 did not inhibit the nerve impulse activity of sensorial neurons as indicated by the lack of a change in response of the contra-lateral paw.

V. Analgesic Effect of Subcutaneous TAFA4 in Animals with Neuropathic Pain

This example illustrates the analgesic effect of TAFA4 on a neuropathic pain model following subcutaneous injection.

V.1. Dose-Effect Study

In order to apprehend the doses which may be tested subcutaneously, a first "fast" test on an inflammatory pain model (1% carrageenan) was conducted on a restricted number of TAFA4-KO mice.

Procedure:

9 eight-week-old male TAFA4-KO mice are used. Recombinant human TAFA4 (#5099-TA, R&D, batch #PXC0213101) is resuspended in 0.9% NaCl at 2 different concentrations (10 µg/mL and 30 µg/mL), for a 10 µl injection per gram. Measurement with Von Frey filaments by the up/down method for determining the baseline. Intraplantar injection of 20 µl of carrageenan (1%) into a hind paw. Measurement of the response threshold, 24 h after injection, followed by subcutaneous blind injection of TAFA4 solution at 2 different concentrations (n=3 at 100 µg/kg; n=3 at 300 µg/kg) or pregabalin solution at 30 mg/kg (n=3), for the experimenter.

Measurement of the response threshold is measured, 30 minutes after injection of the compounds, and subsequently 2 h and 4 h.

Results:

The results are shown in FIG. 11. After injection of carrageenan, the mice developed mechanical allodynia. Injection of pregabalin caused an increase in the response threshold. Similarly, injection of TAFA4 also induced a statistically significant increase in the response threshold at 100 µg/kg and even stronger at 300 µg/kg.

TAFA4 therefore caused an analgesic effect by subcutaneous injection in the carrageenan model.

V.2. Subcutaneous Injection in SNI Animals

Procedure:

The experiments were conducted on eight-week-old male WT C57B16 mice. 48 mice were used. Recombinant human TAFA4 (#5099-TA, R&D, batch #PXC0213101) is resuspended in 0.9% NaCl at 3 different concentrations (3 µg/mL, 10 µg/mL and 30 µg/mL). A 30 µg/mL BSA solution is used as a negative control. After having measured the base threshold of mice with Von Frey filaments by the up/down method, the SNI model is set into place. The mice are anesthetized, ligature of the tibial nerve and fibular nerve is put into practice and these two nerves are then severed. The sural nerve left intact develops neuropathy quite rapidly. The occurrence of neuropathy is ascertained 3 days post-surgery. A decrease in the response threshold to Von Frey filaments of the ipsilateral paw is thereby observed.

7 days after surgery, the response threshold is again measured. 100 µl/10 g of each of the TAFA4 solutions (n=11 at 30 µg/kg; n=12 at 100 µg/kg; n=11 at 300 µg/kg) and of BSA (n=12) are then blind-injected subcutaneously for the experimenter.

The response threshold is measured 1 hour, 2 hours, 4 hours, 6 hours and 24 hours after injection.

Results (FIG. 12):

The subcutaneous injection of TAFA4 induced a strong increase in the response threshold as soon as 1 hour post-injection. This effect was maintained for at least 4 h with the three tested concentrations. As for intrathecal injection, the effect seems to last longer with the higher concentration.

Subcutaneous injection of TAFA4 therefore induces an analgesic effect on mechanical allodynia induced by the SNI neuropathic pain model. The concentration of 300 µg/kg was used for the continuation of the study.

VI. TAFA4 Induces a Sustained Analgesic Effect with No Side Effects

The purpose of these experiments was to further confirm the analgesic effect of TAFA4 by subcutaneous injection in the SNI model, and to check that this effect is maintained and safe by achieving several injection points.

Procedure:

The experiments were conducted on eight-week-old male WT C57B16 mice. 24 mice were used. Recombinant human TAFA4 (#5099-TA, R&D, batch #PXC0213101 and #PXC0214011) is resuspended in 30 µg/mL of 0.9% NaCl. A 30 µg/mL BSA solution is used as a negative control. After having measured the base threshold of mice with Von Frey filaments by the up/down method, the SNI model is set into place. The mice are anesthetized, ligature of the tibial nerve and fibular nerve is put into practice and these two nerves are then severed. The sural nerve left intact develops neuropathy quite rapidly.

7 days after surgery, a decrease of the response threshold to Von Frey filaments of the ipsilateral paw is observed. 10 µl/g of the TAFA4 (300 µg/kg) and BSA solutions are then blind-injected subcutaneously (n=12 for each of the BSA and TAFA4 groups). The response threshold is measured 1 hour, 2 hours, 4 hours and 6 hours after injection. The same experimental procedure is carried out at 7 days, 14 days and 21 days post-surgery.

Results (FIG. 13):

A strong increase in the response threshold to mechanical stimulation was observed following subcutaneous injection of 300 µg/kg of TAFA4 at 7 days, 14 days and 21 days post-surgery. About 40-50% of the initial value (before surgery) may be reached. In the three cases, the effect remained similar (with no significant difference) as indicated by analysis of the areas under the curve.

These results therefore confirm the potent analgesic effect of the TAFA4 protein or agonist of the invention.

Various organs (liver, spleen, kidneys, heart and lungs) of the subcutaneously treated animals were removed and frozen for subsequent studies. The weight of the treated animals was monitored all along the experiment. No difference was observed in the weight curve (FIG. 14). Furthermore, the various removed organs were weighed with precision scales, before being set in 4% paraformaldehyde (PFA) overnight at 4° C., and then incubated in sucrose 30% before being cryogenically kept in OCT at −80° C. No difference was observed in all of the tested organs (liver, spleen, kidneys, heart and lungs) between treated and control animals.

Our results therefore show the effect of a TAFA4 protein in an SNI neuropathic pain model. Mechanical allodynia (decrease in the response threshold) induced by this model may be inhibited by intrathecal or subcutaneous injection of TAFA4. It is important to note that the doses used are low (2 μg intrathecally and 6-8 μg subcutaneously). Further, the response threshold of the contra-lateral paws remained unchanged after injection of TAFA4, thus showing that TAFA4 does not act as an agent blocking nerve impulses.

VII. Conclusions

The present invention demonstrates, for the first time, that TAFA4 protein is involved in the control of pain, and shows its efficiency in the treatment of pain in different pain models.

The invention also shows that TAFA4 is specifically expressed in small-diameter sensory neuron C-LTMRs.

The invention further shows that TAFA4 loss-of-function led to increased injury-induced mechanical and chemical hypersensitivity and enhanced excitability of lamina IIi neurons.

The invention also shows that TAFA4+ afferents exclusively innervate hair follicles in the periphery and project to the innermost layer of lamina II centrally.

The invention shows that TAFA4 modulates neuronal excitability and the threshold of somatic sensation.

The invention further shows that TAFA4 protein can specifically target mechanically and chemically induced nociceptive signals.

The invention also shows that TAFA4 compounds and compositions are capable of activating a new analgesic pathway by modulating C-LTMR-nociceptor-mediated excitability of spinal cord interneurons (preferably lamina IIi interneurons), for example, via modulation of the activity of receptors present on said interneurons (such as potassium ion channels, calcium ion channels or low-density lipoprotein receptors, e.g., LRP1).

The inventors also propose that TAFA4 may regulate presynaptic channels in primary afferents which in turn increase synaptic transmission. Postsynaptically, the "TAFA4ergic" C-LTMR afferents face a network of lamina IIi excitatory glutamatergic and inhibitory GABAergic/glycinergic interneurons that are connected to projection neurons residing in lamina I.

The inventors further show that mechanical and formalin-induced pain hypersensitivity in TAFA4-null mice was reversed to WT levels after administration of the human recombinant TAFA4.

All the experimental data demonstrated by the inventors in the present application also revealed that C-LTMR-derived TAFA4 modulates the second phase of formalin-evoked pain. In particular, the data provided herein show that TAFA4-null mice exhibited exaggerated/enhanced formalin-evoked pain. The inventors propose that formalin-evoked nocifensive behavior could be specifically triggered by C-LTMR sensory neurons.

Genetic marking of TAFA4-expressing neurons allowed detailed in vitro study of the physiological properties of C-LTMRs. Patch-clamp analysis revealed a strikingly homogenous population of neurons with small capacitance, unique short-duration APs, the presence of a TTX resistant Nav1.8 current and a remarkable co-expression of several low threshold currents as well as slowly and ultra-slowly adapting excitatory mechano-gated currents.

By comparing pain phenotypes in wild-type (wt) or TAFA4 null mice, inventors have established the proof of concept that disturbing TAFA4 function causes modulation of neuronal excitability, which contributes to pain signaling. In particular, the inventors have clearly demonstrated that loss of TAFA4 function enhances mechanical and chemical hypersensitivity in a variety of pain models. In conclusion, TAFA4 can be used as an active ingredient for treating pathological pain signaling via modulation of neuronal excitability.

REFERENCES

Basbaum, A. I., Bautista, D. M., Scherrer, G., and Julius, D. (2009). Cellular and molecular mechanisms of pain. Cell 139, 267-284.

Bessou, P., Burgess, P. R., Perl, E. R., and Taylor, C. B. (1971). Dynamic properties of mechanoreceptors with unmyelinated (C) fibers. J Neurophysiol 34, 116-131.

Bennett, G. J., and Xie, Y. K. (1988). A peripheral mononeuropathy in rat that produces disorders of pain sensation like those seen in man. Pain 33, 87-107.

Descoeur, J., Pereira, V., Pizzoccaro, A., Francois, A., Ling, B., Maffre, V., Couette, B., Busserolles, J., Courteix, C., Noel, J., et al. (2011). Oxaliplatin-induced cold hypersensitivity is due to remodelling of ion channel expression in nociceptors. EMBO molecular medicine 3, 266-278.

Hao, J., and Delmas, P. (2010). Multiple desensitization mechanisms of mechanotransducer channels shape firing of mechanosensory neurons. J Neurosci 30, 13384-13395.

Hao, J., and Delmas, P. (2011). Recording of mechanosensitive currents using piezoelectrically driven mechanostimulator. Nature protocols 6, 979-990.

Li, L., Rutlin, M., Abraira, V. E., Cassidy, C., Kus, L., Gong, S., Jankowski, M. P., Luo, W., Heintz, N., Koerber, H. R., et al. (2011). The functional organization of cutaneous low-threshold mechanosensory neurons. Cell 147, 1615-1627.

Moqrich, A., Earley, T. J., Watson, J., Andahazy, M., Backus, C., Martin-Zanca, D., Wright, D. E., Reichardt, L. F., and Patapoutian, A. (2004). Expressing TrkC from the TrkA locus causes a subset of dorsal root ganglia neurons to switch fate. Nat Neurosci 7, 812-818.

Moqrich, A., Hwang, S. W., Earley, T. J., Petrus, M. J., Murray, A. N., Spencer, K. S., Andahazy, M., Story, G. M., and Patapoutian, A. (2005). Impaired thermosensation in mice lacking TRPV3, a heat and camphor sensor in the skin. Science 307, 1468-1472.

Mourot, A., Fehrentz, T., Le Feuvre, Y., Smith, C. M., Herold, C., Dalkara, D., Nagy, F., Trauner, D., and Kramer, R. H. (2012). Rapid optical control of nociception with an ion-channel photoswitch. Nat Methods 9, 396-402.

Seal, R. P., Wang, X., Guan, Y., Raja, S. N., Woodbury, C. J., Basbaum, A. I., and Edwards, R. H. (2009). Injury-induced mechanical hypersensitivity requires C-low threshold mechanoreceptors. Nature 462, 651-655.

Todd, A. J. (2010). Neuronal circuitry for pain processing in the dorsal horn. Nat Rev Neurosci 11, 823-836.

Tang T., Y., Emtage, P., Funk, W. D., Hu, T., Arterburn, M., Park, E. E., and Rupp, F. (2004). TAFA: a novel secreted family with conserved cysteine residues and restricted expression in the brain. Genomics 83, 727-734.

Woodbury, C. J., Ritter, A. M., and Koerber, H. R. (2001). Central anatomy of individual rapidly adapting low-threshold mechanoreceptors innervating the "hairy" skin of newborn mice: early maturation of hair follicle afferents. J Comp Neurol 436, 304-323.

The invention claimed is:

1. A method of treating pain in a subject, the method comprising administering a TAFA4 protein to a subject having pain, wherein said TAFA4 protein comprises SEQ ID NO: 1 or comprises a sequence having at least 90% identity to SEQ ID NO: 1.

2. The method according to claim 1, wherein said TAFA4 protein is administered to the subject intramuscularly, intravenously, intraperitoneally, orally, anally, cutaneously, subcutaneously, dermally, transdermally or intrathecally.

3. The method according to claim 1, wherein the dose of TAFA4 protein is between 1 µg and 100 mg/kg/day.

4. The method according to claim 1, wherein said TAFA4 protein is used in combination with at least one additional active compound efficient against pain.

5. The method according to claim 1, wherein said subject is a mammal.

6. The method according to claim 1, wherein said pain is a neuropathic pain, an inflammatory pain, a nociceptor-mediated pain, an acute pain, a subacute pain, a chronic pain, a somatic pain, a visceral pain, allodynia, hyperalgesia, or a pain associated with a nerve injury.

7. The method according to claim 1, wherein the subject is a human and the pain is a neuropathic pain, an inflammatory pain, a nociceptor-mediated pain, an acute pain, a subacute pain, a chronic pain, a somatic pain, a visceral pain, allodynia, hyperalgesia, or a pain associated with a nerve injury.

8. The method according to claim 1, wherein the pain is neuropathic pain, the subject is a human, and the TAFA4 protein comprises SEQ ID NO: 1 or comprises a sequence having at least 90% identity to SEQ ID NO: 1.

9. The method according to claim 1, wherein the pain is chronic inflammatory pain, the subject is a human, and the TAFA4 protein comprises SEQ ID NO: 1 or a comprises a sequence having at least 90% identity to SEQ ID NO: 1.

10. The method according to claim 1, wherein said TAFA4 protein comprises a sequence having at least 90% identity to SEQ ID NO: 1.

* * * * *

UNITED STATES PATENT AND TRADEMARK OFFICE
CERTIFICATE OF CORRECTION

PATENT NO. : 9,884,088 B2
APPLICATION NO. : 14/787483
DATED : February 6, 2018
INVENTOR(S) : Aziz Moqrich, Marie-Claire Delfini and Annabelle Mantilleri Page 1 of 1

It is certified that error appears in the above-identified patent and that said Letters Patent is hereby corrected as shown below:

In the Specification

Column 4,
Line 41, "D34" should read --IB4--.
Line 48, "T-type $Ca^{2+}$," should read --T-type $Ca^{2+}$-,--.

Column 6,
Line 29, "and 5100" should read --and S100--.

Column 20,
Line 6, "(IuS, 1000" should read --(IuS, ≥1000--.
Lines 43-44, "(7-11 S2)" should read --(7-11 Ω)--.

Signed and Sealed this
Twenty-third Day of April, 2019

Andrei Iancu
*Director of the United States Patent and Trademark Office*

(12) SUPPLEMENTAL EXAMINATION CERTIFICATE

United States Patent
Moqrich et al.

(10) Number: US 9,884,088 F1
(45) Certificate Issued: Jun. 9, 2022

Control No.: 96/050,004

Filing Date: May 6, 2022

Primary Examiner: Padmashri Ponnaluri

No substantial new question of patentability is raised in the request for supplemental examination. See the Reasons for Substantial New Question of Patentability Determination in the file of this proceeding.

(56) Items of Information

OTHER DOCUMENTS

1. Declaration of Aziz Moqrich under 37 CFR 1.132 dated March 2, 2022 (Annex 1) (herein "The Moqrich Declaration").

2. Pages 10, 11 and 42-47 of U.S. Application No. 14/787,483. (Annex 2) (herein "The '483 application pages 10, 11, 42-47").

3. Sequence listing of U.S. Application No. 14/787,483. (Annex 3) (herein "The '483 application sequence listing").

4. Tang et al., "TAFA: a novel secreted family with conserved cysteine residues and restricted expression in the brain." Genomics, 2004, pp. 727-734, vol. 83. (Annex 4) (herein "Tang").